US009855296B2

(12) United States Patent
Cataldo et al.

(10) Patent No.: US 9,855,296 B2
(45) Date of Patent: Jan. 2, 2018

(54) METHODS AND COMPOSITIONS FOR MITOCHONDRIAL REPLACEMENT THERAPY

(71) Applicant: The McLean Hospital Corporation, Belmont, MA (US)

(72) Inventors: Anne M. Cataldo; Bruce M. Cohen, Lexington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 9 days.

(21) Appl. No.: 15/353,347

(22) Filed: Nov. 16, 2016

(65) Prior Publication Data

US 2017/0065635 A1  Mar. 9, 2017

Related U.S. Application Data

(63) Continuation of application No. 12/598,287, filed as application No. PCT/US2008/005627 on May 2, 2008.

(60) Provisional application No. 60/927,240, filed on May 2, 2007.

(51) Int. Cl.
```
A61K 35/12      (2015.01)
A01K 67/027     (2006.01)
C12N 9/12       (2006.01)
G01N 33/68      (2006.01)
A61K 9/00       (2006.01)
A61K 45/06      (2006.01)
A61K 35/00      (2006.01)
```

(52) U.S. Cl.
CPC .......... *A61K 35/12* (2013.01); *A01K 67/0271* (2013.01); *A01K 67/0276* (2013.01); *A61K 9/0019* (2013.01); *A61K 45/06* (2013.01); *C12N 9/1252* (2013.01); *G01N 33/6896* (2013.01); *A01K 2207/15* (2013.01); *A01K 2217/00* (2013.01); *A01K 2217/05* (2013.01); *A01K 2217/075* (2013.01); *A01K 2227/105* (2013.01); *A01K 2267/0356* (2013.01); *A61K 35/00* (2013.01)

(58) Field of Classification Search
None
See application file for complete search history.

(56) References Cited

U.S. PATENT DOCUMENTS

| 2001/0021526 A1 | 9/2001 | Davis et al. |
| 2002/0049176 A1 | 4/2002 | Anderson et al. |
| 2004/0248286 A1 | 12/2004 | Konradi et al. |
| 2005/0164933 A1 | 7/2005 | Tymianski et al. |
| 2006/0147925 A1 | 7/2006 | Morley et al. |
| 2006/0241034 A1 | 10/2006 | Chauvier et al. |
| 2007/0155826 A1 | 7/2007 | Smith-Swintosky et al. |
| 2011/0008310 A1 | 1/2011 | Cataldo et al. |

FOREIGN PATENT DOCUMENTS

| WO | WO-2004/100773 A2 | 11/2004 |
| WO | WO-2005/103229 A2 | 11/2005 |

OTHER PUBLICATIONS

Akbarzadeh et al., "Liposome: classification, preparation, and applications," Nanoscale Res Lett. 8(1):102 (2013) (9 pages).
Bainbridge, "Understanding and coping with mitochondrial disease," Hamilton Health Sciences, McMaster Children's Hospital (2010) (38 pages).
Banks, "Characteristics of compounds that cross the blood-brain barrier," BMC Neurol. 9(Suppl 1):S3 (2009) (5 pages).
Bressert, "Treatment of bipolar disorder (manic depression)," http://psychcentral.com/lib/treatment-of-bipolar-disorder-manic-depression, accessed Aug. 3, 2015 (2 pages).
Choi et al., "Analysis of proteome bound to D-loop region of mitochondrial DNA by DNA-linked affinity chromatography and reverse-phase liquid chromatography/tandem mass spectrometry," Ann N Y Acad Sci. 1042:88-100 (2005).
Cummins, "Mitochondria: Potential Roles in Embryogenesis and Nucleocytoplasmic Transfer," Hum. Reprod. Update. 7(2):217-28 (2001).
Dahl et al., "Mitochondrial diseases: beyond the magic circle," Am J Med Genet. 106(1):1-3 (2001).
Extended European Search Report for European Application No. 13172945.1, dated Aug. 20, 2013 (14 pages).
Extended European Search Report for PCT/US2008/005627, dated Sep. 1, 2011.
International Preliminary Report on Patentability (PCT/US2008/005627), dated Nov. 3, 2009.
International Search Report (PCT/US2008/005627), dated Jul. 21, 2008.
Kidd, "Neurodegeneration from Mitochondrial Insufficiency: Nutrients, Stem Cells, Growth Factors, and Prospects for Brain Rebuilding Using Integrative Management," Altern. Med. Rev. 10:268-293, 2005.
Konradi et al., "Molecular evidence for mitochondrial dysfunction in bipolar disorder," Arch Gen Psychiatry. 61(3):300-8 (2004).
Liu et al., "Effect of Mitochondrial Transplantation from Cumulus Granular Cells to the Early Embryos of Aged Mice," Journal of Reproduction & Contraception 19:211-217 (2008).
Masuzawa et al., "Transplantation of autologously derived mitochondria protects the heart from ischemia-reperfusion injury," Am J Physiol Heart Circ Physiol. 304(7):H966-82 (2013).
McCully et al., "Injection of isolated mitochondria during early reperfusion for cardioprotection," Am J Physiol Heart Circ Physiol. 296(1):H94-H105 (2009).
McCully et al., "Mitochondrial transplantation for cardioprotection," Circulation 116:II_496 (2007).

(Continued)

*Primary Examiner* — Suzanne M Noakes
*Assistant Examiner* — Stephen Chong
(74) *Attorney, Agent, or Firm* — Clark & Elbing LLP

(57) ABSTRACT

The invention features methods, kits, and compositions for mitochondrial replacement in the treatment of disorders arising from mitochondrial dysfunction. The invention also features methods of diagnosing neuropsychiatric (e.g., bipolar disorder) and neurodegenerative disorders based on mitochondrial structural abnormalities.

20 Claims, 11 Drawing Sheets

(56) References Cited

OTHER PUBLICATIONS

Medical Research Council "*Research in Focus*—Therapeutic Use of Cell Nuclear Replacement: Therapeutic Cloning," 2002.
Oklan, "Mitochondrial dysfunction in neuropsychiatric disorders," accessed May 5, 2013 (8 pages).
Pinkert et al., "Mitochondria transfer into mouse ova by microinjection," Transgenic Res. 6(6):379-83 (1997).
Rossignol et al., "Mitochondrial Threshold Effects," Biochem. J. 370:751-762, 2003.
Spees et al., "Mitochondrial Transfer Between Cells Can Rescue Aerobic Respiration," Proc. Natl. Acad. Sci. USA 103:1283-1288, 2006.
Stork et al., "Mitochondrial Dysfunction in Bipolar Disorder: Evidence from Magnetic Resonance Spectroscopy Research," Molecular Psychiatry 10:900-919 (2005).
Tarnopolsky, "MITO 101—Supplements and Nutrition," United Mitochondrial Disease Foundation, 2005, available <http://umdf.org/atf/cf/%7B28038c4c-02ee-4ad0-9db5-d23e9d9f4d45%7D/supplements%20and%20nutrition%20-%tarnopolsky.pdf> (6 pages).
Türker et al., "Nasal route and drug delivery systems," Pharm World Sci. 26(3):137-42 (2004).
Van Blerkom et al., "Mitochondrial Transfer between Oocytes: Potential Applications of Mitochondrial Donation and the Issue of Heteroplasmy," Hum. Reprod. 13:2857-2868, 1998.
Yi et al., "Mitochondria Transfer Can Enhance the Murine Embryo Development," J. Assist Reprod. Genet. 24:445-449 (2007).

Active Mitochondria Isolated From Adult Bone Marrow Derived Stem Cells

Mitochondrial Transplantation in Human Fibroblasts

Figure 3
Fig. 3A
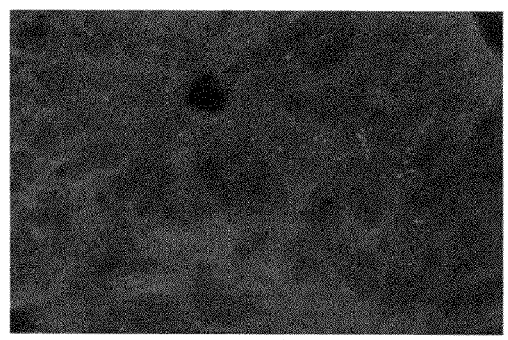
Fig. 3B
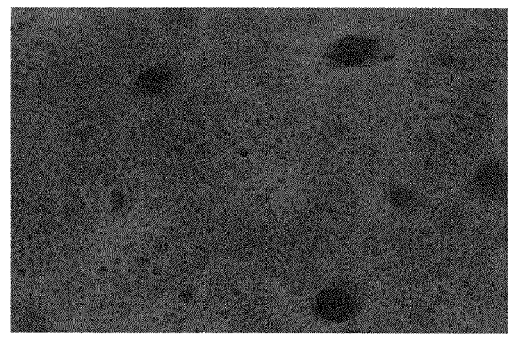
Fig. 3C

Fig. 4A                    Fig. 4B

METHODS AND COMPOSITIONS FOR MITOCHONDRIAL REPLACEMENT THERAPY

BACKGROUND OF THE INVENTION

Mitochondria are essential organelles in plant and animal cells that arise from a prokaryotic ancestor and play a key role in processes such as oxidative phosphorylation, aerobic metabolism of glucose and fat, calcium signaling, and apoptosis (Wallace, *Proc. Natl. Acad. Sci. USA* 91:8739 (1994) and Dyall et al., *Science* 304:253 (2004)). The human mitochondrial genome is 16,568 bp and encodes a limited number of mitochondria-specific proteins, rRNAs, and tRNAs (Brandon et al., *Nucleic Acids Res.* 33:D611 (2005)). All other mitochondrial proteins are encoded in the nucleus. The mitochondrial genome is maternally inherited and undergoes a high rate of mutation because mtDNA is not protected by histones, is inefficiently repaired (Mason et al., *Nucleic Acids Res.* 31:1052 (2003)), and is exposed to oxygen radicals generated by oxidative phosphorylation (Wallace, *Proc. Natl. Acad. Sci. USA* 91:8739 (1994)).

A large number of heritable diseases are caused by mutations that are found in mitochondrial and nuclear genes encoding mitochondrial proteins and that produce heritable skeletal or cardiac myopathies (Wallace, *Proc. Natl. Acad. Sci. USA* 91:8739 (1994), Brandon et al., *Nucleic Acids Res.* 33:D611 (2005), Wallace, *Science* 283:1482 (1999), and Green et al., *Science* 305:626 (2004)). In addition, environmentally-induced mutations in mtDNA have been implicated in many common acquired disorders, including ischemic diseases of the heart and brain, neurodegenerative diseases, some liver diseases, and some cancers (Wallace, *Science* 283:1482 (1999)). For example, disorders involved in mitochondrial dysfunction affecting cellular processes include but are not limited to neuropsychiatric diseases such as bipolar disorder (BD), depression, schizophrenia, and Rett's syndrome; neurodegenerative disease like Alzheimer's disease, Parkinson's disease, Friedreich's ataxia (and other ataxias); amyotrophic lateral sclerosis (ALS) (and other motor neuron diseases); Huntington's disease; and various neuropathies and myopathies, such as Leber's hereditary optic neuropathy (LHON), encephalopathy, lactacidosis, stroke (MELAS); myoclonic epilepsy with ragged red fibers (MERFF); macular degeneration; epilepsy; and mitochondrial myopathy.

The use of antioxidants targeted to mitochondria, which has been shown to be effective at slowing disease progression, has been reported by Jauslin et al., (*FASEB J.* 17:1972 (2003)). Therapeutic benefit of administering γ-tocopherol derivatives and metabolites as antioxidants and nitrogen oxide scavengers which treat high blood pressure, thromboembolic diseases, cardiovascular disease, cancer, natriuretic disease, formation of neuropathological lesions and reduced immune system response are disclosed in U.S. Pat. Nos. 6,555,575; 6,242,479; 6,150,402; and 6,410,589. The use of certain chroman derivatives in cosmetic and dermatological preparations is disclosed in U.S. Patent Publication No. 2002/0127252. The beneficial effects of Vitamin E in the progression of a number of major degenerative diseases of the nervous system has been examined in Fryer, *Nutritional Neuroscience* 1:327 (1998).

Numerous attempts have been made to treat disease associated with mitochondrial dysfunction using transplanted tissues or cells. Attempts to treat such diseases with replacement cells can be complicated by the necessity of replacing diseased tissue rather than improving the function of existing cells and tissue.

The present invention addresses the need for new therapies for conditions characterized by mitochondrial dysfunction without the replacement of existing cells. The invention also features methods of diagnosing neuropsychiatric (e.g., bipolar disorder) and neurodegenerative disorders based on mitochondrial structural abnormalities.

SUMMARY OF THE INVENTION

Applicants have discovered methods, kits, and compositions for mitochondrial replacement in the treatment of disorders arising from mitochondrial dysfunction. Applicants also have discovered methods of diagnosing neuropsychiatric (e.g., bipolar disorder) and neurodegenerative disorders associated with mitochondrial dysfunction based on mitochondrial structural abnormalities.

Accordingly, in a first aspect the invention features a method for implanting mitochondria in vivo into cells of a subject by administering to the subject isolated and substantially pure mitochondria.

In a related aspect, the invention features a method for increasing the respiratory ability of a cell in a subject by administering to the subject isolated and substantially pure mitochondria in an amount sufficient to increase the respiratory ability of the cell.

In another aspect, the invention features a method of improving muscle function in a subject by administering to the subject isolated and substantially pure mitochondria in an amount sufficient to improve muscle function.

The invention further features a method of treating a condition associated with mitochondrial dysfunction in a subject in need thereof by administering to the subject isolated and substantially pure mitochondria in an amount sufficient to treat the condition.

In an embodiment of the methods of the invention, the methods include the steps of (i) separating mitochondria from other constituents of a cell to produce isolated and substantially pure mitochondria; and (ii) administering the isolated and substantially pure mitochondria into the subject. In certain embodiments, the cells are progenitor cells or any other cell type described herein.

The isolated and substantially pure mitochondria can be administered systemically (e.g., intranasally, intramuscularly, subcutaneously, or intravenously) or can be administered locally. The route of administration used in the methods of the invention can be any route described herein.

In still other embodiments of the methods of the invention, the methods further include administering to the subject one or more agents selected from vitamin A, vitamin C, vitamin D, vitamin E, vitamin K, folic acid, choline, vitamin B1, vitamin B2, vitamin B5, vitamin B6, vitamin B12, biotin, nicotinamide, betacarotene, coenzyme Q, selenium, superoxide dismutase, glutathione peroxide, uridine, creatine succinate, pyruvate, dihydroxyacetone), acetyl-L-carnitine, alpha-lipoic acid, cardiolipin, omega fatty acid, lithium carbonate, lithium citrate, calcium, and mixtures thereof, such as the cocktails described herein.

In another aspect, the invention features a pharmaceutical composition including (i) isolated and substantially pure mitochondria; (ii) a pharmaceutically acceptable excipient; and (iii) one or more compounds selected from vitamin A, vitamin C, vitamin D, vitamin E, vitamin K, folic acid, choline, vitamin $B_1$, vitamin $B_2$, vitamin $B_5$, vitamin $B_6$, vitamin $B_{12}$, biotin, nicotinamide, betacarotene, coenzyme Q, selenium, superoxide dismutase, glutathione peroxide, uridine, creatine succinate, pyruvate, dihydroxyacetone), acetyl-L-carnitine, alpha-lipoic acid, cardiolipin, omega fatty acid, lithium carbonate, lithium citrate, calcium, and mixtures thereof, such as the cocktails described herein.

In still another aspect, the invention features a kit including (i) isolated and substantially pure mitochondria and (ii) instructions for administering said mitochondria to a subject.

The invention also features a kit including (i) isolated and substantially pure mitochondria and (ii) instructions for administering said mitochondria to a subject for the treatment of a condition associated with mitochondrial dysfunction.

In an embodiment of the kits of the invention, the kits include mitochondria formulated with a pharmaceutically acceptable excipient and one ore more compounds selected from vitamin A, vitamin C, vitamin D, vitamin E, vitamin K, folic acid, choline, vitamin $B_1$, vitamin $B_2$, vitamin $B_5$, vitamin $B_6$, vitamin $B_{12}$, biotin, nicotinamide, betacarotene, coenzyme Q, selenium, superoxide dismutase, glutathione peroxide, uridine, creatine succinate, pyruvate, dihydroxyacetone), acetyl-L-carnitine, alpha-lipoic acid, cardiolipin, omega fatty acid, lithium carbonate, lithium citrate, calcium, and mixtures thereof, such as the cocktails described herein.

In any of the above aspects, the mitochondria can be syngeneic mitochondria, allogeneic mitochondria, or xenogeneic mitochondria. The mitochondria for use in the methods, kits, and compositions of the invention can be obtained from any source described herein.

In any of the above aspects, the condition associated with mitochondrial dysfunction can be selected from, without limitation, a neurodegenerative disorder (e.g., Friedrich's ataxia, amyotrophic lateral sclerosis, mitochondrial myopathy, encephalopathy, lactacidosis, stroke (MELAS), myoclonic epilepsy with ragged red fibers (MERFF), epilepsy, Parkinson's disease, Alzheimer's disease, or Huntington's Disease), a neuropsychiatric disorder (e.g., bipolar disorder, schizophrenia, depression, addiction disorders, anxiety disorders, attention deficit disorders, personality disorders, autism, or Asperger's disease), diabetes, metabolic disease, an ocular disorder associated with mitochondrial dysfunction (e.g., glaucoma, diabetic retinopathy or age-related macular degeneration), an ischemia related condition (e.g., a condition resulting from vascular occlusion, tachycardia, hypotension, or sickle cell disease), aging, mitochondrial toxicity associated with therapeutic agents, or migraine. The condition associated with mitochondrial dysfunction can be any condition, disease, or disorder described herein.

In another aspect, the invention features a method of diagnosing a neuropsychiatric or neurodegenerative disorder associated with mitochondrial dysfunction in a subject by (i) determining whether mitochondria within a cell present in a tissue sample extracted from the subject contain a mitochondrial structural abnormality; and (ii) if the mitochondrial structural abnormality exists, diagnosing the subject as having, or being at risk of developing, the disorder.

In a related aspect, the invention features a method of diagnosing a neuropsychiatric or neurodegenerative disorder associated with mitochondrial dysfunction in a subject by (i) identifying whether a subject is at risk of having or developing the disorder; and (ii) determining whether mitochondria within a cell present in a tissue sample extracted from the subject contain a mitochondrial structural abnormality characteristic of the disorder.

The invention further features a method of diagnosing a neuropsychiatric or neurodegenerative disorder associated with mitochondrial dysfunction by (i) identifying whether a mitochondrial structural abnormality exists in a cell present in a tissue sample extracted from the subject; and (ii) on the basis of the results of step (i), reporting to a physician whether the subject has a mitochondrial structural abnormality characteristic of the disorder.

In the diagnostic methods of the invention the neuropsychiatric or neurodegenerative disorder associated with mitochondrial dysfunction can be, for example, a neuropsychiatric disorder selected from bipolar disorder, schizophrenia, depression, addiction disorders, anxiety disorders, attention deficit disorders, personality disorders, autism, Asperger's disease, and any other neuropsychiatric disorder described herein. In certain embodiments, the neuropsychiatric or neurodegenerative disorder associated with mitochondrial dysfunction can be, for example, a neurodegenerative disorder selected from Friedrich's ataxia, amyotrophic lateral sclerosis, mitochondrial myopathy, encephalopathy, lactacidosis, stroke (MELAS), myoclonic epilepsy with ragged red fibers (MERFF), epilepsy, Parkinson's disease, Alzheimer's disease, Huntington's Disease, and any other neurodegenerative disorder described herein.

In certain embodiments of the diagnostic methods of the invention, the tissue sample extracted from the subject does not include nervous tissue. For example, the tissue sample can be, without limitation, a blood sample. The cell extracted from the tissue sample can be, for example, a lymphocyte (e.g., a T cell, B cell, or NK cell), or a fibroblast.

In the diagnostic methods of the invention the mitochondrial structural abnormality can include, without limitation, one or more of the following: mitochondrial perinuclear aggregation or clustering, reduced presence or absence of mitochondria in the cellular periphery, reduced average mitochondrial perinuclear distance, increased mitochondrial clustering, punctate, cup-shaped or ring-shaped mitochondria, longer or condensed mitochondrial profiles that include large intercristae spaces and narrow junctions between cristae, and reduced mitochondrial branching.

As used herein, the term "isolated and substantially pure mitochondria" refers to a composition containing mitochondria separated from other cellular constituents in which the combined mass of the non-mitochondrial cellular constituents are less than 5%, 4%, 3%, 2%, 1%, 0.5%, or 0.1% of the mass of the mitochondria in the isolated and substantially pure mitochondria-containing composition. Mitochondria can be isolated and purified using any methods known in the art, including those described herein.

As used herein, the term "neurodegenerative disorder" refers to diseases of the nervous system (e.g., the central nervous system or peripheral nervous system) characterized by abnormal cell death. Examples of neurodegenerative disorders include Alzheimer disease, Down's syndrome, Frontotemporal dementia, Niemann-Pick's disease, Parkinson's disease, Huntington's disease (HD), dentatorubropallidoluysian atrophy, Kennedy's disease (also referred to as spinobulbar muscular atrophy), and spinocerebellar ataxia (e.g., type 1, type 2, type 3 (also referred to as Machado-Joseph disease), type 6, type 7, and type 17)), fragile X (Rett's) syndrome, fragile XE mental retardation, Friedreich's ataxia, myotonic dystrophy, spinocerebellar ataxia type 8, and spinocerebellar ataxia type 12, Alexander disease, Alper's disease, amyotrophic lateral sclerosis, ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, ischemia stroke, Krabbe disease, Lewy body dementia, multiple sclerosis, multiple system atrophy, Pelizaeus-Merzbacher disease, Pick's disease, primary lateral sclerosis, Refsum's disease, Sandhoff disease, Schilder's disease, spinal cord injury, spinal muscular atrophy, Steele-Richardson-Olszewski disease, and Tabes dorsalis.

By "neuropsychiatric disorder" is meant disorders of the nervous system by both neurologic and psychiatric abnormalities. Neuropsychiatric disorders include, without limitation, bipolar disorder; schizophrenia; affective disorders, such as depression, addictive disorders, anxiety disorders, attentional disorders, and personality disorders; and disorders of childhood development, such as autism and Asperger's disease.

As used herein, the term "ischemia related condition" refers to conditions characterized by insufficient blood supply to a tissue or organ and which can result in damage or dysfunction of the tissue or organ (e.g., heart, brain, intestine, liver, kidney, muscle, and eye), and can be due to any number of causes including, for example, vascular occlusion (caused by, e.g., athero-arteriosclerosis, plaque formation or thrombosis), tachycardia, hypotension, sickle cell disease, or other injury).

"Marrow-derived adult progenitor cells" or "MAPCs" refer to a population of specialized mesenchymal cells in the adult bone marrow that give rise to mesoderm, endoderm, neuroectoderm, and skin, and exhibit many of the same traits as embryonic stem cells.

Mitochondria for use in the methods, kits, and compositions of the invention can be obtained from a variety of sources and can be classified according to the genetic relationship between the mitochondrial source and the subject being treated. As used herein, "allogeneic mitochondria" refers to mitochondria obtained from same species, but a different genotype than that of the subject receiving treatment; "syngeneic mitochondria" refers to mitochondria obtained from same species and having the same genotype as that of the subject receiving treatment; and "xenogeneic mitochondria" refers to mitochondria obtained a different species than the subject being treated.

By "mitochondrial structural abnormalities" is meant any morphological or spatial characteristic in a mitochondrion, or distribution characteristic of mitochondria within a cell, that is not observed in the cells (e.g., fibroblasts or lymphocytes) of healthy subjects. Abnormalities can occur in a single mitochondrion, or in the spatial grouping or arrangement of a plurality of mitochondria within a cell. Mitochondrial structural abnormalities include, but are not limited to, mitochondrial perinuclear aggregation or clustering, increased mitochondrial clustering, punctate, cup- or ring-shaped mitochondria, longer or condensed mitochondrial profiles that include large intercristae spaces and narrow junctions between cristae, and reduced mitochondrial branching.

By "perinuclear aggregation" or "perinuclear clustering" is meant an abnormal distribution of mitochondria within a cell characterized by a reduction in the mitochondrial numerical density at the periphery of the cell (e.g., 60-100 μm from the nucleus) in comparison to the distribution observed in a cell from a healthy subject (see FIG. 8e).

As used herein, "identifying a subject at risk" refers to identifying a subject in need of a diagnosis, or confirmation of a diagnosis, as having, or being likely to develop, a neuropsychiatric or neurodegenerative disorder associated with mitochondrial dysfunction. Such a subject is identified using methods other than those described herein (i.e., methods that do not include assessing whether the cells of the subject include mitochondrial structural abnormalities). Any one or more of a variety of techniques known in the art can be used. For example, a subject at risk may be identified by symptoms exhibited by the subject, by genetic testing, and/or by family history. The diagnostic methods of the invention can be used, alone or in combination with these other methods, to diagnose (or to confirm a diagnosis of) a neuropsychiatric or neurodegenerative disorder associated with mitochondrial dysfunction in a subject at risk of having or developing such a condition.

"Treating" and "treatment" refer to reduction in severity, progression, spread, and/or frequency of symptoms, elimination of symptoms and/or underlying cause, prevention of the occurrence of symptoms and/or their underlying cause, and improvement or remediation of damage. "Treatment" is meant to include therapeutic treatment as well as prophylactic, or suppressive measures for the condition, disease or disorder.

As used herein, the terms "an amount sufficient" and "sufficient amount" refer to the amount of isolated and substantially pure mitochondria of the invention required to treat or prevent a condition associated with mitochondrial dysfunction. The sufficient amount used to practice the invention for therapeutic or prophylactic treatment of conditions caused by or contributed to by mitochondrial dysfunction can vary depending upon the manner of administration, the age, body weight, and general health of the subject. Ultimately, the attending physician will decide the appropriate amount and dosage regimen. Such amount is referred to as a "sufficient" amount.

By "subject" is meant any animal (e.g., a human). Other animals that can be treated using the methods, compositions, and kits of the invention include horses, dogs, cats, pigs, goats, rabbits, hamsters, monkeys, guinea pigs, rats, mice, lizards, snakes, sheep, cattle, fish, and birds.

By "pharmaceutical composition" is meant a composition containing isolated and substantially pure mitochondria formulated with a pharmaceutically acceptable excipient, and which is manufactured and marketed in compliance with the requirements of a governmental regulatory agency as part of a therapeutic regimen for the treatment or prevention of disease in a mammal. Pharmaceutical compositions can be formulated, for example, for intravenous administration (e.g., as a suspension of mitochondria in a solvent system suitable for in vivo injection), or any other formulation and for any other route of administration described herein.

"Increasing respiratory ability" refers to increasing the efficiency of coupling between phosphorylation and oxygen consumption in a cell. An increase in respiratory ability can be observed by measuring in vivo $O_2$ consumption and ATP synthesis rates using the methods described in Marcinek, *Acta Physiologica Scandinavica* 182: 343 (2004) before and after mitochondrial replacement therapy.

Other features and advantages of the invention will be apparent from the following detailed description, the drawings, and the claims.

BRIEF DESCRIPTION OF THE DRAWINGS

FIG. 2b). Mitochondria from human BD fibroblasts show an altered morphology consisting of short, thickened profiles that are arranged in a predominantly perinuclear location compared to age-matched controls. The transplantation of healthy mitochondria to BD fibroblasts restores the normal mitochondrial distribution and morphologic phenotype (see FIG. 2c vs. FIG. 2d).

FIG. 3 is a photograph depicting (FIG. 3a) the distribution of liposome packaged mitochondria in adult mouse liver. Yellow fluorescent protein (YFP)-tagged mitochondrial isolates were obtained fresh from normal human fibroblasts infected with a replication defective herpes simplex viral (HSV) 1 vector encoding a fusion of YFP and a human mitochondrial targeting sequence. Animals were injected one time intravenously with 150 µl of purified mitochondrial pellet suspended in saline; (FIG. 3b) liver distribution of liposome packaged mitochondria after intramuscular administration; and (FIG. 3c) liver distribution of liposome vehicle (without mitochondria) after intramuscular administration (no fluorescence is observed). The systemic administration of mitochondria results in uptake of mitochondria by cells of the liver.

(FIG. 4b) brain distribution of liposome packaged mitochondria after intramuscular administration. The systemic administration of mitochondria results in uptake by cells of the brain.

FIGS. 5a and 5c, bar=2 µm; FIGS. 5b and 5d, bar=500 nm; FIG. 5b right inset and 5e, bar=500 nm; FIG. 5b left inset and 5d inset, bar=1 µm; and FIGS. 5f-h, bar=500 nm.

FIG. 7a-d, bar=10 µm; FIG. 7e-h, bar=10 µm.

FIG. 8e: Morphometric analysis of spatial distribution in mitochondria identified in fibroblasts with Mitotracker 7510 (green, arrows) from normal controls (n=6) (see FIG. 8a) and patients with BD (n=6) (see FIGS. 8b and e left panel, arrow). Concentric annuli the shape of each nuclear envelope were placed at the centroids of each nucleus (FIG. 8e, middle panel, "bull's eye" for a single cell) to cover the spatial extents of each fibroblast. Our image segmentation algorithm measured mitochondrial numerical density objectively as a function of perinuclear distance from the envelope on the logarithmic scale (FIG. 8e, right panel, for an example BD and healthy control cell); raw data were too noisy to display for all cells, images and subjects to reveal any suspected density gradients in the ensemble. However, all BD cells exhibited positive mitochondrial densities at a maximum perinuclear distance of 60 µm, as shown; for all healthy cells this maximum distance was 100 µm, as shown. Our random effects analysis of covariance, that included the main effects of perinuclear distance, diagnostic group and the group by distance interaction, revealed the suspected underlying mitochondrial density differences between the BD and healthy control groups. The BD group exhibited significantly less decline in numerical densities at perinuclear distances proximal to the nuclear envelope than those seen in healthy subjects (ANCOVA t-value 2.62, p=0.008). FIG. 8a-e, bar=10 µm.

FIGS. 9a and b, bar=50 µm; FIGS. 9c and d, bar=10 µm. ATP levels measured by luciferase assay (FIG. 9e) shows 2.4-fold lower levels of ATP in fibroblasts from subjects with BD (n=6) compared to healthy control fibroblasts (n=6) (Control fibroblasts, no treatment— mean=$9.02\times10^{-4}$, SE $2.3\times10^{-4}$; BD fibroblasts, no treatment—mean=$3.8\times10^{-4}$, SE $5.4\times10^{-5}$; p<0.05). FIGS. 9a and b, bar=50 µm; FIGS. 9c and d, bar=10 µm.

FIG. 10a-h, bar=10 µm.

FIG. 11a-g, bar=10 µm.

DETAILED DESCRIPTION OF THE INVENTION

Figure 1:
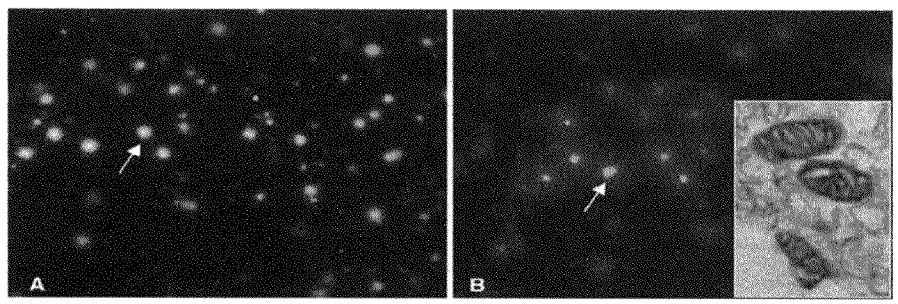
FIG. 1 is a photograph depicting active mitochondria isolated from adult bone marrow derived cells.

Applicants have identified methods, kits, and compositions for mitochondrial replacement in the treatment of conditions arising from, or accompanied by, mitochondrial dysfunction. Applicants further provide methods for diagnosing neuropsychiatric and neurodegenerative disorders associated with mitochondrial dysfunction based on mitochondrial structural abnormalities.

Conditions associated with mitochondrial dysfunction can result in the progressive mosaic appearance of cells with defective electron transport activity in muscle, with cells almost devoid of cytochrome c oxidase (COX) activity interspersed randomly amidst cells with normal activity, and a higher incidence of COX-negative cells in biopsies (e.g., in older subjects). The organism, during aging, or in a variety of conditions associated with mitochondrial dysfunction, is thus faced with a situation in which irreplaceable post-mitotic cells (e.g., neurons, skeletal and cardiac muscle) must be preserved and their function maintained to a significant degree, in the face of an inexorable progressive decline in mitochondrial respiratory chain function. Neurons with dysfunctional mitochondria become progressively more sensitive to insults like excitotoxic injury. Mitochondrial failure contributes to most degenerative diseases (especially neurodegeneration) that accompany aging. Congenital mitochondrial diseases often involve early-onset neurodegeneration similar in fundamental mechanism to disorders that occur during aging of people born with normal mitochondria. The methods, kits, and compositions of the invention allow for the replacement of dysfunctional mitochondria in these irreplaceable post-mitotic cells, allowing for the rescue or improvement of the mitochondrial function in these cells.

Mitochondria are involved in a strikingly diverse range of disease processes. Primary genetic disorders fall into two broad classes: those with deficiencies in either nuclear or mitochondrial genes (see Sholte, *J. Bioenerg. Biomembr.* 20:161 (1988), reporting over 60 human diseases with defects in nuclear genes encoding mitochondrial functions). Mitochondrial dysfunction is also recognized as a contributor to common diseases with multi-factorial pathogenesis. Some examples are given below, concluding with the condition of aging, which has a clear relationship to oxidative stress of mitochondrial origin.

Conditions Associated with Mitochondrial Dysfunction

Conditions associated with mitochondrial dysfunction include those in which deficits in mitochondrial respiratory chain activity contribute to the development of pathophysiology of such diseases or disorders in a mammal. This includes (1) congenital genetic deficiencies in the activity of one or more components of the mitochondrial respiratory or electron transport chain; and (2) acquired deficiencies in the levels or activities of one or more components of the mitochondrial respiratory chain, wherein such deficiencies are caused by (a) oxidative damage during aging; (b) elevated intracellular calcium; (c) exposure of affected cells to nitric oxide; (d) hypoxia or ischemia; (e) microtubule-associated deficits in axonal transport of mitochondria, or (f) expression of mitochondrial uncoupling proteins.

Common symptoms of mitochondrial dysfunction include cardiomyopathy, muscle weakness and atrophy, developmental delays (involving motor, language, cognitive or executive function), ataxia, epilepsy, renal tubular acidosis, peripheral neuropathy, optic neuropathy, autonomic neuropathy, neurogenic bowel dysfunction, sensorineural deafness, neurogenic bladder dysfunction, dilating cardiomyopathy, migraine, hepatic failure, lactic acidemia, and diabetes mellitus.

Neuropsychiatric Disorders

The brain requires ten fold the energy on average of the rest of the body. Many neuropsychiatric disorders may be associated with abnormalities of energy production or mitochondrial dysfunction, in particular. Neuropsychiatric disorders include, without limitation bipolar disorder (BD), schizophrenia, depression, anxiety disorders, attention deficit disorders, addictive disorders, personality disorders, autism and Asperger's disease. The methods, kits, and compositions of the invention can be used for the treatment of neuropsychiatric disorders.

Neurodegenerative Disorders

The methods, kits, and compositions of the invention can be used for the treatment of neurodegenerative disorders. Many progressive neurological diseases result from the execution of neurons by mitochondrial apoptosis. Friedrich's ataxia results from a genetic defect in the frataxin gene, which is involved in mitochondrial iron transport (Babcock et al., *Science* 276:1709 (1997)); human deafness dystonia results from a defect in a small component of the mitochondrial protein import machinery (Koehler et al., *Proc. Natl. Acad. Sci. USA* 96:2141 (1999)); one well-characterized cause of amyotrophic lateral sclerosis is deficiency in Cu—Zn superoxide dismutase, which is located in the mitochondrial intermembrane space as well as the cytoplasm (Deng et al., *Science* 261:1047 (1993)). The discovery that several environmental toxins cause Parkinsonism by inhibiting respiratory complex I and promoting the generation of reactive oxygen species has made this complex a focus for research on the basis of Parkinson's disease (Dawson et al., *Science* 302:819 (2003)). More recently, the mitochondrial protein encoded by PINK 1 has provided a direct link between mitochondria and Parkinson's disease (Valente et al., *Science* 304:1158 (2004)). Alzheimer's disease is also linked to mitochondrial toxicity through the mitochondrial protein ABAD, a target of amyloid (Lustbader et al., *Science* 304:448 (2004)). Huntington's Disease has been associated with defects in energy metabolism that appear to be widespread, affecting both the brain and peripheral tissues, and arising from mitochondrial dysfunction (Leegwater-Kim et al., *NeuroRx* 1:128 (2004)). A basic abnormality involved in the pathogenesis of bipolar disorder (BD) is believed to involve energy production and in particular, mitochondrial activity. Evidence from many sources, including, postmortem, genetic, brain imaging and peripheral cell studies support energy deficits and mitochondrial dysfunction as one important causative factor in the development of BD (see Hough et al., *Bipolar Disord.* 2:145 (2000), Fattal et al., *Psychosomatics* 47:1 (2006), and Kato et al., *Bipolar Disord.* 2:180 (2000)).

Diabetes and Metabolic Disease

The methods, kits, and compositions of the invention can be used for the treatment of diabetes and metabolic disease. The central role of mitochondria in metabolism of carbohydrates and fatty acids gives this organelle an important function in diabetes (Maechler et al., *Nature* 414:807 (2001)). A mouse knockout of an abundant mitochondrial transcription factor has provided a model for 13-cell ablation in juvenile diabetes (Silva et al., *Nat. Genet.* 26:335 (2000)). Mutations in mtDNA and in PPARγ, a master regulator of mitochondrial biogenesis, are correlated with type II diabetes. Insulin release depends on mitochondrial function as influenced by the expression of the membrane transporter UCP2 (Petersen et al., *Science* 300:1140 (2003); Zhang et al., *Cell* 105:745 (2001)). The activity of thiazolidinediones as antidiabetic agents appears to depend on their ability to serve as ligands for PPARγ and its co-activator, PGC-1, in their control of expression of nuclear genes for mitochondrial gene products (Mootha et al., *Nature Genet* 34:267 (2003); Puigserver et al., *Endocr. Rev.* 24:78 (2003)).

Mitochondrial Toxicity of Therapeutic Agents

The methods, kits, and compositions of the invention can be used for the treatment of toxicity associated with therapeutic agents. The past few decades have witnessed significant progress in development of chemotherapeutic agents for cancer and viral diseases. In the case of conventional cancer chemotherapy, the goal of selectively killing tumor cells has been difficult to attain due to collateral toxicity to normal cells. Cancer chemotherapeutic agents delivered to damage nuclear DNA also directly damage mtDNA as well, even in "resting tissues" where nuclear DNA replication is inactive, but mtDNA replication continues. Mitochondria are poorly equipped to repair this sort of collateral damage (Bhatia et al., *Nature Reviews Cancer* 2:124 (2002)). Nucleoside analogues used as either anticancer or antiviral agents can also have significant mitochondrial toxicity. The best known examples include the inhibition of DNA polymerase y by AZT and dideoxynucleosides used to target the related HIV reverse transcriptase and the fatal hepatotoxicity of fialuridine observed when this agent was tested for activity against hepatitis B virus (Lewis et al., *Nat. Med.* 1:417 (1995)). In addition, the myopathy and rhabdomyolysis associated with the popular cholesterol-lowering statins (Thompson et al., *JAMA* 289:1681 (2003)) are believed to involve interference with mitochondrial ubiquinone biosynthesis. Accordingly, the mitochondrial replacement methods, kits, and compositions of the invention can be used to ameliorate the toxicity of drugs. Pharmaceutical agents associated with mitochondrial toxicity include reverse transcriptase inhibitors (e.g., azidothymidine (AZT), stavudine (D4T), zalcitabine (ddC), didanosine (DDI), fluoroiodoarauracil (FIAU), lamivudine (3TC), and abacavir), protease inhibitors (e.g., ritonavir, indinavir, saquinavir, nelfinavir), and inhibitors of dihydroorotate dehydrogenase DHOD (e.g., leflunomide, and brequinar), among others.

Migraine

The methods, kits, and compositions of the invention can be used for the treatment of migraine. Metabolic studies on patients with recurrent migraine headaches indicate that deficits in mitochondrial activity are commonly associated with this disorder, manifesting as impaired-oxidative phosphorylation and excess lactate production. Such deficits are not necessarily due to genetic defects in mitochondrial DNA. Migrainers are hypersensitive to nitric oxide, an endogenous inhibitor of cytochrome c oxidase. In addition, patients with mitochondrial cytopathies, e.g., MELAS, often have recurrent migraines.

Ocular Disorders Associated with Mitochondrial Dysfunction

The methods, kits, and compositions of the invention can be used for the treatment of ocular disorders, such as glaucoma, diabetic retinopathy and age-related macular degeneration. Retinal damage is attributed to free radical initiated reactions in glaucoma, diabetic retinopathy and age-related macular degeneration (AMD). The eye is a part of the central nervous system and has limited regenerative capability. The retina is composed of numerous nerve cells which contain the highest concentration of polyunsaturated fatty acids (PFA) and subject to oxidation. Free radicals are generated by UV light entering the eye and mitochondria in the rods and cones, which generate the energy necessary to transform light into visual impulses. Free radicals cause peroxidation of the PFA by hydroxyl or superoxide radicals which in turn propagate additional free radicals. The free radicals cause temporary or permanent damage to retinal tissue.

Glaucoma is usually viewed as a disorder that causes an elevated intraocular pressure (IOP) that results in permanent damage to the retinal nerve fibers, but a sixth of all glaucoma cases do not develop an elevated IOP. This disorder is now perceived as one of reduced vascular perfusion and an increase in neurotoxic factors. Recent studies have implicated elevated levels of glutamate, nitric oxide and peroxynitirite in the eye as the causes of the death of retinal ganglion cells.

Diabetic retinopathy occurs when the underlying blood vessels develop microvascular abnormalities consisting primarily of microaneurysms and intraretinal hemorrhages. Oxidative metabolites are directly involved with the pathogenesis of diabetic retinopathy and free radicals augment the generation of growth factors that lead to enhanced proliferative activity. Nitric oxide produced by endothelial cells of the vessels may also cause smooth muscle cells to relax and result in vasodilation of segments of the vessel. Ischemia and hypoxia of the retina occur after thickening of the arterial basement membrane, endothelial proliferation and loss of pericytes. The inadequate oxygenation causes capillary obliteration or nonperfusion, arteriolar-venular shunts, sluggish blood flow and an impaired ability of RBCs to release oxygen. Lipid peroxidation of the retinal tissues also occurs as a result of free radical damage.

Ischemia Related Conditions

The methods, kits, and compositions of the invention can be used for the treatment of ischemia related conditions. Oxygen deficiency results in both direct inhibition of mitochondrial respiratory chain activity by depriving cells of a terminal electron acceptor for cytochrome c reoxidation at Complex IV, and indirectly, especially in the nervous system, via secondary post-anoxic excitotoxicity and nitric oxide formation. In conditions like cerebral anoxia, angina or sickle cell anemia crises, tissues are relatively hypoxic. In such cases, an increase in mitochondrial activity provides protection of affected tissues from deleterious effects of hypoxia, attenuate secondary delayed cell death, and accelerate recovery from hypoxic tissue stress and injury. The methods, kits, and compositions of the invention can be useful for preventing delayed cell death (apoptosis in regions like the hippocampus or cortex occurring about 2 to 5 days after an episode of cerebral ischemia) after ischemic or hypoxic insult, for example, to the brain.

Muscle Function

The methods, kits, and compositions of the invention can be used for enhancing muscle performance. For example, the methods, kits, and compositions of the invention may be useful for improving physical endurance (e.g., ability to perform a physical task such as exercise, physical labor, sports activities, etc.), inhibiting or retarding physical fatigues, enhancing blood oxygen levels, enhancing energy in healthy individuals, enhance working capacity and endurance, reducing muscle fatigue, reducing stress, enhancing cardiac and cardiovascular function, improving sexual ability, increasing muscle ATP levels, and/or reducing lactic acid in blood.

Enhanced sports performance, strength, speed and endurance are typically measured by an increase in muscular contraction strength, increase in amplitude of muscle contraction, shortening of muscle reaction time between stimulation and contraction, the ability to overcome muscle fatigue, and ability to maintain activity for longer periods of time. Aside from muscle performance during endurance exercise, free radicals and oxidative stress parameters are affected in pathophysiological states. A substantial body of data now suggests that oxidative stress contributes to muscle wasting or atrophy in pathophysiological states (see Clarkson, *Crit. Rev. Food Sci. Nutr.* 35:31 (1995); and Powers et al., *Proc. Nutr. Soc.* 58:1025 (1999)). For example, in muscular dystrophies dystrophin-glycoprotein complex (DGC) defects suggest that one mechanism of cellular injury is functional ischemia related to alterations in cellular NOS and disruption of a normal protective action of NO. Rando (*Microsc. Res. Tech.* 55:223 (2001)) has shown that oxidative injury precedes pathologic changes and that muscle cells with defects in the DGC have an increased susceptibility to oxidant challenges. Excessive lipid peroxidation due to free radicals has also been shown to be a factor in myopathic diseases such as McArdle's disease (see Russo et al., *Med. Hypotheses.* 39:147 (1992)). Furthermore, mitochondrial dysfunction is a well-known correlate of age-related muscle wasting (sarcopenia) and free radical damage has been suggested, though poorly investigated, as a contributing factor (see Navarro et al., *Front. Biosci.* 6:D26 (2001)). Other indications include acute sarcopenia, for example muscle atrophy and/or cachexia associated with burns, bed rest, limb immobilization, or major thoracic, abdominal, and/or orthopedic surgery. The methods of the present invention can be effective in the treatment of muscle related pathological conditions.

Aging

The methods, kits, and compositions of the invention can be used for the treatment of aging and conditions associated therewith. During normal aging, there is a progressive decline in mitochondrial respiratory chain function. Beginning about age 40, there is an exponential rise in accumulation of mitochondrial DNA defects in humans, and a concurrent decline in nuclear-regulated elements of mitochondrial respiratory activity. Many mitochondrial DNA lesions have a selection advantage during mitochondrial turnover, especially in post-mitotic cells. The proposed mechanism is that mitochondria with a defective respiratory chain produce less oxidative damage to themselves than do mitochondria with intact functional respiratory chains (mitochondrial respiration is the primary source of free radicals in the body). Therefore, normally-functioning mitochondria accumulate oxidative damage to membrane lipids more rapidly than do defective mitochondria, and are, therefore, "tagged" for degradation by the autophagic and lysosomal systems. Since mitochondria within cells have a half life of about 10 days, a selection advantage can result in rapid replacement of functional mitochondria with those with diminished respiratory activity, especially in slowly dividing cells. The net result is that once a mutation in a gene for a mitochondrial protein that reduces oxidative damage to mitochondria occurs, such defective mitochondria will rapidly populate the cell, diminishing or eliminating its respiratory capabilities. The inexorable decline of mitochondrial function with age contributes to the aging-related conditions of neurodegeneration, and type II diabetes. Just as oxidative stress underlies some of these defined diseases, it is thought to contribute to generalized aging (Harman, *Proc. Natl. Acad. Sci. USA* 78:7124 (1981)). Mutations in *C. elegans* and *D. melanogaster* that reduce mitochondrial oxidative stress have been shown to prolong lifespan in these organisms (Hekimi et al., *Science* 299:1351 (2003)). Moreover, mammals maintained on calorie-restricted diets have a reduced metabolic rate that is thought to contribute to significantly increased longevity. Numerous studies have documented an increase in point mutations and deletions in mtDNA with advancing age. Furthermore, Trifunovic et al. have recently showed that mice engineered to express an error prone mitochondrial DNA polymerase can serve as an excellent model for premature ageing (*Nature* 429:417 (2004)).

Isolation of Mitochondria

The key steps when isolating mitochondria from any tissue or cell are typically: (i) rupturing of cells by mechanical and/or chemical means, (ii) differential centrifugation at low speed to remove debris and extremely large cellular organelles, and (iii) centrifugation at a higher speed to isolate and collect and substantially pure mitochondria. Suggested amounts of starting material and expected mitochondria yields are shown in Table 1 for rodent tissues.

TABLE 1

| Sample | Starting Material (wet weight) | Expected Yield |
|---|---|---|
| Rodent liver | 0.3-0.5 g | 2-4 mg |
| Rodent heart* | 0.2-0.4 g | 1-2 mg |
| Rodent brain | 0.3-0.4 g | 4-5 mg |

*Hard tissues result in lower yields due to difficult homogenization.

Buffers and samples should be chilled where possible.

Mitochondria integrity can be tested by screening for cytochrome c, porin, or cyclophilin D in the isolated mitochondria versus in the supernatant fraction (i.e., using commercially available antibody kits—see, for example, those available from MitoSciences®). While isolated mitochondria for use in the methods, kits, and compositions of the invention can be obtained from any allogeneic, syngeneic, or xenogeneic source, it is often desirable to extract the mitochondria for use in the methods, kits, and compositions of the invention from progenitor cells.

Progenitor Cells

Desirably, the cells from which mitochondria are isolated for use in the methods, kits, and compositions of the invention are undifferentiated marrow-derived adult progenitor cells (MAPCs). The isolation of MAPCs is well known in the art (see, for example, Gartner et al., *Proc. Nat. Acad. Sci. USA* 77:4756 (1980); Mauney et al., *Tissue Engin.* 10:81 (2004); Sutherland et al., *Proc. Nat. Acad. Sci. USA* 87:3584 (1990); Ramshaw et al., *Exp. Hematol.* 29:981 (2001); Kassem, *Ann. NY Acad. Sci.* 1067:436 (2006); Sotiropoulou et al., *Stem Cells* 24:1409 (2006); Romanov et al., *Bull Exp. Biol. Med.* 140:138 (2005); Alhadlaq et al., *Stem Cell Dev.* 13:436 (2004); Hung et al., *Stem Cells* 20:249 (2002); Tondeau et al., *Cytotherapy* 6:372 (2004); Smith et al., *Stem Cells* 22:823 (2004); Baxter et al., *Stem Cells* 22:675 (2004); Jones et al., *Arthritis Rheum.* 46:3349 (2002); and Prockop et al., *Cytotherapy* 3:393 (2001)).

Alternatively, the cells from which mitochondria are isolated can be selected from neural stem cells, muscle stem cells, satellite cells, liver stem cells, hematopoietic stem cells, bone marrow stromal cells, epidermal stem cells, embryonic stem cells, mesenchymal stem cells, umbilical cord stem cells, precursor cells, muscle precursor cells, myoblast, cardiomyoblast, neural precursor cells, glial precursor cells, neuronal precursor cells, hepatoblasts, neurons, oligodendrocytes, astrocytes, Schwann cells, skeletal muscle cells, cardiomyocytes, or hepatocytes. Immortalized cells can also be used as a) source.

The source of cells for mitochondrial isolation can be the patient to be treated him or herself, a relative, an unrelated donor or a donor of another species. Once isolated, mitochondria can be cultured, and these cultured mitochondria can also be used in the mitochondrial replacement therapy described herein.

Mitochondrial Replacement Therapy

Formulation

The pharmaceutical compositions and kits of the invention may contain pharmaceutically acceptable excipients for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), See Remington's Pharmaceutical Sciences (18th Ed., A. R. Gennaro, ed., Mack Publishing Company 1990).

For example, lipids may be used in the present invention as a carrier in the formulation of isolated and purified mitochondria of the invention. The lipids may be natural, synthetic or semisynthetic (i.e., modified natural). Lipids useful in formulating the compositions of the invention, without limitation, fatty acids, lysolipids, oils (including safflower, soybean and peanut oil), phosphatidylcholine with both saturated and unsaturated lipids, including phosphatidylcholine; dioleoylphosphatidylcholine; dimyristoylphosphatidylcholine; dipentadecanoylphosphatidylcholine, dilauroylphosphatidylcholine, dioleoylphosphatidylcholine, dipalmitoylphosphatidylcholine; and distearoylphosphatidylcholine; phosphatidylethanolamines, such as dioleoylphosphatidylethanolamine; phosphatidylserine; phosphatidylglycerol; phosphatidylinositol, sphingolipids, such as sphingomyelin; glycolipids, such as ganglioside GM1 and GM2; glucolipids; sulfatides; glycosphingolipids; phosphatidic acid; palmitic acid; stearic acid; arachidonic acid; oleic acid; lipids bearing polymers such as polyethyleneglycol, chitin, hyaluronic acid or polyvinylpyrrolidone; lipids bearing sulfonated mono-, di-, oligo- or polysaccharides; cholesterol, cholesterol sulfate and cholesterol hemisuccinate; tocopherol hemisuccinate, lipids with ether and ester-linked fatty acids, polymerized lipids (a wide variety of which are known in the art), diacetyl phosphate, stearylamine, cardiolipin, phospholipids with short chain fatty acids of about 6 to about 8 carbons in length, synthetic phospholipids with asymmetric acyl chains (e.g., with one acyl chain of about 6 carbons and another acyl chain of about 12 carbons), 6-(5-cholesten-3b-yloxy)-1-thio-β-D-galactopyranoside, digalactosyldiglyceride, 6-(5-cholesten-3.beta.-yloxy)hexyl-6-amino-6-deoxy-1-thio-β-D-galacto pyranoside, 6-(5-cholesten-3.beta.-yloxy)hexyl-6-amino-6-deoxyl-1-thio-.alpha.-D-manno pyranoside, 12-(((7'-diethylaminocoumarin-3-yl)carbonyl)methylamino)-octadecanoic acid; N-[12-(((7'-diethylaminocoumarin-3-yl)carbonyl)methylamino)octadecanoyl]-2-aminopalmitic acid; (cholesteryl)4'-trimethyl-ammonio)butanoate; N-succinyldioleoylphosphatidylethanolamine; 1,2-dioleoyl-sn-glycerol; 1,2-dipalmitoyl-3-succinyl-glycerol; 1,3-dipalmitoyl-2-succinylglycerol; 1-hexadecyl-2-palmitoyl-glycerophosphoethanolamine; palmitoylhomocysteine; and combinations thereof. Vesicles or other structures may be formed of the lipids, either as monolayers, bilayers, or multilayers and may or may not have a further coating. Vesicles or other lipid structures used as carriers can further include, e.g., peptides, polypeptides, glycoproteins, or other constituents useful for the generation, viability, or targeting of such carriers. For example, vesicles bearing a protein ligand can be used to specifically target cells that express a cognate receptor to facilitate targeted application of the purified mitochondria of the invention.

Cationic lipids and other derivatized lipids and lipid mixtures also may be useful as carriers for use in the methods, kits, and compositions of the invention. Suitable cationic lipids include dimyristyl oxypropyl-3-dimethylhydroxy ethylammonium bromide (DMRIE), dilauryl oxypropyl-3-dimethylhydroxy ethylammonium bromide (DLRIE), N-[1-(2,3-dioleoyloxyl)propal]-n,n,n-trimethylammonium sulfate (DOTAP), dioleoylphosphatidylethanolamine (DOPE), dipalmitoylethylphosphatidylcholine (DPEPC), dioleoylphosphatidylcholine (DOPC), polylysine, lipopolylysine, didoceyl methylammonium bromide (DDAB), 2,3-dioleoyloxy-N-[2-(sperminecarboxamidoethyl]-N,N-dimethyl-1-propanamin ium trifluoroacetate (DOSPA), cetyltrimethylammonium bromide (CTAB), lysyl-PE, 3.beta.-[N,(N',N'-dimethylaminoethane)-carbamoyl]cholesterol (DC-Cholesterol, also known as DC-Chol), (-alanyl cholesterol, N-[1-(2,3-dioleoyloxy)propyl]-N,N,N-trimethylammonium chloride (DOTMA), dipalmitoylphosphatidylethanolamine-5-carboxyspermylamide (DPPES), dicaproylphosphatidylethanolamine (DCPE), 4-dimethylaminopyridine (DMAP), dimyristoylphosphatidylethanolamine (DMPE), dioleoylethylphosphocholine (DOEPC), dioctadecylamidoglycyl spermidine (DOGS), N-[1-(2,3-dioleoyloxy)propyl]-N-[1-(2-hydroxyethyl)]-N,N-dimethylammonium iodide (DOHME), Lipofectin (DOTMA+DOPE, Life Technologies, Inc., Gaithersburg, Md.), Lipofectamine (DOSPA+DOPE, Life Technologies, Inc., Gaithersburg, Md.), Transfectace (Life Technologies, Inc., Gaithersburg, Md.), Transfectam (Promega Ltd., Madison, Wis.), Cytofectin (Life Technologies Inc., Gaithersburg, Md.). Other representative cationic lipids include but are not limited to phosphatidylethanolamine, phospatidylcholine, glycero-3-ethylphosphatidylcholine and fatty acyl esters thereof, di- and trimethyl ammonium propane, di- and tri-ethylammonium propane and fatty acyl esters thereof. A preferred derivative from this group is N-[1-(2,3-dioleoyloxy)propyl]-N,N,N-trimethylammonium chloride (DOTMA). Additionally, a wide array of synthetic cationic lipids function as compounds useful in the invention. These include common natural lipids derivatized to contain one or more basic functional groups. Examples of lipids which may be so modified include but are not limited to dimethyldioctadecylammonium bromide, sphingolipids, sphingomyelin, lysolipids, glycolipids such as ganglioside GMl, sulfatides, glycosphingolipids, cholesterol and cholesterol esters and salts, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidyl-ethanolamine and palmitoylhomocystiene.

The methods, kits, and compositions of the invention can include the formulation of mitochondria with one or more agents (e.g., vitamins, antioxidants, acetyl-L-carnitine, alpha-lipoic acid, cardiolipin, fatty acids, lithium carbonate, lithium citrate, calcium, or s-adenosyl-L-methionine) or mixtures thereof, such as those described herein.

The mitochondria for use in the methods, compositions, and kits of the invention can be packaged in unit dosage forms, for example in vials, ampoules, pre-filled syringes, or sachets.

Administration

The formulations can be administered to human subjects in therapeutically effective amounts. Typical dose ranges are from about 1 mg/kg to about 10 g/kg of body weight. The preferred dosage of isolated and substantially pure mitochondria to be administered is likely to depend on such variables as the type and extent of the disorder, the overall health status of the particular subject, the specific compound being administered, the excipients used to formulate the mitochondria, and its route of administration. Standard clinical trials maybe used to optimize the dose and dosing frequency for any condition and route of administration.

For systemic administration, isolated and substantially pure mitochondria can be, without limitation, administered by intranasal, intravenous, intra-arterial, subcutaneous, or intramuscular routes. The mitochondria can be administered alone (e.g., as a monotherapy), subsequent to pretreatment with one of several second agents described herein, or in combination with one of several second agents described herein (e.g., either formulated together and administered simultaneously, or formulated separately and administered within 2 hours of each other).

For the treatment of conditions associated with localized mitochondrial dysfunction (e.g., ocular disorders, neurodegenerative disorders, neuropsychiatric disorders, and other localized tissues) it may be desirable to administer the isolated and substantially pure mitochondria locally. Local routes of administration include, without limitation, local injection, intracranial, intracerebroventricular, intracerebral, intraorbital, ophthalmic, intraventricular, intracapsular, intraspinal, intrathecal, intracisternal, intraperitoneal, intranasal, or topical administration. For example, the isolated and substantially pure mitochondria can be administered directly into discrete areas or nuclei of the brain, e.g., the rostral ventromedial medulla (RVM) or a brain ventricle, or onto the dura mater.

Combination Therapy

Isolated and substantially pure mitochondria can be used in combination with a second agent selected from vitamins (e.g., vitamin A, vitamin C, vitamin D, vitamin E, vitamin K, folic acid, choline, vitamin $B_1$, vitamin $B_2$, vitamin $B_5$, vitamin $B_6$, and vitamin $B_{12}$, biotin, nicotinamide), antioxidants (e.g., betacarotene, coenzyme Q, selenium, superoxide dismutase, glutathione peroxide, uridine, catalase, creatine succinate, pyruvate, dihydroxyacetone), acetyl-L-carnitine, alpha-lipoic acid, cardiolipin, fatty acids (e.g., omega-3 fatty acids or omega-6 fatty acids), lithium carbonate, lithium citrate, calcium, and s-adenosyl-L-methionine. These additional agents can be directly administered to the patient (e.g., orally or intravenously) and formulated together with the isolated and substantially pure mitochondria or formulated and administered separately.

Abnormalities in Mitochondrial Structure

Neurons and glia in the prefrontal cortices of postmortem brain from patients with BD display abnormalities in mitochondrial morphology and intracellular distribution. These alterations are also exhibited in primary skin fibroblasts and lymphocytes obtained from living patients. Under basal metabolic conditions, these structural abnormalities exist in the absence of detectable changes in ATP levels or loss of mitochondrial membrane potential. However, metabolic stress, promoted by treatment with hydrocortisone or hydrogen peroxide, resulted in decreased ATP levels and loss of mitochondrial membrane potential that was greater in cells from patients with BD than healthy controls. Also, these treatments caused alterations in mitochondrial structure and distribution in control cells resembling those seen in untreated cells from individuals with BD. Our results are consistent with evidence linking reduced energy production and mitochondrial dysfunction to BD. Whether (1) alterations in mitochondrial shape and distribution are the underlying cause of energy dysfunction in BD, (2) structural abnormalities of mitochondria are secondary to mitochondrial dysfunction and impaired energy metabolism evoked by neuroendocrine, oxidative, or possibly other stresses, or (3) both altered mitochondrial structure and function are epiphenomena associated with an independent dysfunction of specific cell types in BD is unknown. Regardless, the mitochondrial abnormalities identified here have broad implications for cell plasticity, resilience, and survival in patients with BD, and can be used as a pathognomic marker for bipolar disorder and other neuropsychiatric and neurodegenerative disorders associated with mitochondrial dysfunction.

Our findings are consistent across three different tissues—brain, fibroblasts and lymphocytes—from two different tissue collections. The structural abnormalities observed were only seen in the tissues from diseased individuals (e.g., individuals with BD) and were associated with a functional difference consistent with those observed in previous brain imaging and tissue studies in patients. Not all of the subjects were receiving the same medications, and the abnormality could not be replicated by exposure of cells in vitro to the medication the subjects most commonly received (i.e., lithium). This suggests, that the effect is a concomitant of illness rather than a consequence of treatment.

Both in postmortem brain and primary fibroblasts and lymphocytes from living individuals with BD, striking morphologic abnormalities of mitochondria were observed. Similar alterations in mitochondrial structure and arrangement have been associated with an imbalance in mitochondrial fission and fusion events, which are concomitants of a wide range of cellular functions including energy metabolism (Escobar-Henriques et al., *Biochim. Biophys. ACTA* 1763:422-429 (2006), Logan et al., *J. Exp. Bot.* 57:1225-1243 (2006), McBride et al., *Curr. Biol.* 16:R551-R560 (2006), and Mannella, *Biochim. Biophys. ACTA* 1762:140-147 (2006)).

As a high user of energy, the brain may be particularly disadvantaged by any dysfunction of mitochondria. Considerable evidence suggests that mitochondrial fission and fusion events may be involved in maintaining mitochondrial transport and delivery to cellular sites requiring high energy demands (Chan, *Cell* 125:1241-1252 (2006), Logan et al., *J. Exp. Bot.* 57:1225-1243 (2006), McBride et al., *Curr. Biol.* 16:R551-R560 (2006), Mannella, *Biochim. Biophys. ACTA* 1762:140-147 (2006), Bossy-Wetzel et al., *Curr. Opin. Cell Biol.* 15:706-716 (2003), and Zanna et al., *Brain* 131:352-367 (2008)), which in neurons and supporting glia is particularly important and, if impaired, could lead to cellular compromise or degeneration (Chan, *Cell* 125:1241-1252 (2006), Logan et al., *J. Exp. Bot.* 57:1225-1243 (2006), McBride et al., *Curr. Biol.* 16:R551-R560 (2006), and Mannella, *Biochim. Biophys. ACTA* 1762:140-147 (2006), and Bossy-Wetzel et al., *Curr. Opin. Cell Biol.* 15:706-716 (2003)). Permeability changes in the outer mitochondrial membrane evoked by cortisol or oxidative damage leading to collapse of membrane potential, release of cytochrome C and other apoptotic mitochrondrial proteins and caspase activation have been shown to initiate apoptotic cell death (Beal, *Free Rad. Biol.* 32:797-803 (2002), Chan, *Cell* 125:1241-1252 (2006), Frederick et al., *J. Cell Biol.* 167:87-98 (2004), Bossy-Wetzel et al., *Curr. Opin. Cell Biol.* 15:706-716 (2003), and Koopman et al., *Am. J. Physiol. Cell Physiol.* 288:C1440-C1450 (2005)). While we did not see evidence of apoptosis in peripheral cells, such events could occur during brain development. Therefore, it is possible that abnormal mitochondrial function underlies cellular abnormalities such as the reduced glial density consistently observed in BD subjects in several post mortem studies of prefrontal cortex, a highly energy dependent region of brain.

Bipolar disorder is most often recurrent and episodes are most likely to occur during periods of stress, with attendant hormonal responses. Changes in mitochondrial bioenergetics have been linked to metabolic stress (Chan, *Cell* 125:1241-1252 (2006), Rossignol et al., *Cancer Res.* 64:985-993 (2004), Escobar-Henriques et al., *Biochim. Biophys. ACTA* 1763:422-429 (2006), Logan et al., *J. Exp. Bot.* 57:1225-1243 (2006), McBride et al., *Curr. Biol.* 16:R551-R560 (2006), Koopman et al., *Am. J. Physiol. Cell Physiol.* 288:C1440-C1450 (2005), Naydenov et al., *Arch. Gen. Psychiatr.* 64:555-564 (2007), and Kato et al., *Bipolar Disord.* 2:180-190 (2000)). Our results show that mitochondrial stress induced by hydrocortisone or oxidative damage using $H_2O_2$ can induce morphologic features, i.e., mitochondrial aggregation, in control cells resembling, at least in part, those seen in untreated cells from patients with BD. In cells from healthy individuals, these changes in mitochondrial morphology were not accompanied by detectable alterations in mitochondrial function (i.e., reduced ATP levels or loss of mitochondrial membrane potential) suggesting that the degree of stress induced dysfunction is not sufficient to disrupt energy metabolism. However, fibroblasts from individuals with BD, which are accompanied by alterations in mitochondrial shape and distribution under basal conditions, when treated with hydrocortisone or $H_2O_2$, exhibit an impaired mitochondrial stress response characterized by reduced levels of ATP and loss of membrane potential. These dysfunctions in energy metabolism may be factors which precipitate alterations in mitochondrial shape and arrangement. Alternatively, structurally abnormal mitochondria may be unable to adapt to conditions of increased energy demand when cells are stressed.

Cumulatively, our findings show that changes in mitochondrial shape and distribution are a consistent feature of neurons and primary non-neuronal cells from individuals with BD. These changes are not seen in tissue from healthy control subjects under basal conditions. Prominent functional alterations of mitochondria were not observed in cells from BD subjects. Thus, structural abnormalities preceded evidence of abnormal mitochondrial function. Mitochondrial stress induced with hydrocortisone or $H_2O_2$ induced BD-like mitochondrial changes in morphology in control cells. In cells from patients with BD exposure to such stressors was accompanied by reduced ATP levels and loss in mitochondrial membrane potential. Our findings suggest that the mitochondrial changes in cells from patients with BD represent morphological antecedents to functional changes which are evoked with cell stress when neuroprotective mechanisms are impaired, resulting in abnormal energy metabolism. These findings also support the possibility that alterations in mitochondrial structure and function may play a role in neuronal and or glial compromise or cell loss in BD.

EXAMPLES

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1

Mitochondrial Replacement Therapy

Mitochondrial Preparation and Structural/Functional Analyses

Mitochondrial isolates can be generated from normal skin fibroblasts using gradient centrifugation (Choi et al., *Ann NY Acad Sci* 1042:88 (2005)). Because metabolic enzyme activities are thought to be different in neuronal and astrocytic mitochondria, undifferentiated marrow-derived adult progenitor cells (MAPCs), which can transdifferentiate into neurons or glia, can be used as a source of mitochondria. We have generated pure preparations of actively respiring mitochondria from both cell types in preliminary studies. Purity and morphological characteristics of the isolates can be determined by electron microscopy. Functional respiratory integrity (proton cycling, oxygen consumption) can be evaluated with specific fluorescent probes, polarimetrically by oxygen electrode, and by cytochrome C oxidase activity. Mitochondrial electron transport chain complexes I-III and ATP synthase (complex V) can be quantified by Western blotting. ATP can be measured by luciferin-luciferase assay. Evidence of apoptosis can be provided by light and electron microscopic examination using standard techniques. Mitochondrial isolates from healthy cells can be delivered by e.g., lipid micelles, to the cultured cell and animal models described below. Cell and animal models receiving vehicle-containing micelles can be used as additional controls.

Formulation

Mitochondrial isolates from healthy cells can be delivered by e.g., lipid micelles, lipid rafts, or clathrin-coated vesicles. Isolates will be obtained from fresh normal healthy cell types and purified by established gradient centrifugation (see above). Purity of mitochondrial isolates and mitochondrial activity will be confirmed as described above. Donor isolates will be packaged using standard transfection protocol in inert, lipid micelles (Lipofectamine 2000® or equivalent) and will be stored no longer than 5 days at 4° C.

The mitochondria can be stored or administered with one of several "cocktails" depending upon the specific deficit to be addressed in the condition to be treated. These cocktails can include vitamins (e.g., vitamin A, vitamin C, vitamin D, vitamin E, vitamin K, folic acid, choline, vitamin $B_1$, vitamin $B_2$, vitamin $B_5$, vitamin $B_6$, and vitamin $B_{12}$, biotin, nicotinamide), antioxidants (e.g., betacarotene, coenzyme Q, selenium, superoxide dismutase, glutathione peroxide, uridine, catalase, creatine succinate, pyruvate, dihydroxyacetone), acetyl-L-carnitine, alpha-lipoic acid, cardiolipin, fatty acids (e.g., omega-3 fatty acids or omega-6 fatty acids), lithium carbonate, lithium citrate, calcium, and s-adenosyl-L-methionine. Cocktails useful in the methods, kits, and compositions of the invention are provided in Table 2.

TABLE 2

| mixture | Components[1] |
|---------|---------------|
| Mix 1 | biotin, acetyl-L-carnitine, alpha-lipoic acid, calcium |
| Mix 2 | acetyl-L-carnitine, alpha-lipoic acid, vitamins |
| Mix 3 | acetyl-L-carnitine, alpha-lipoic acid, antioxidants |
| Mix 4 | acetyl-L-carnitine, alpha-lipoic acid, vitamins, cardiolipin |
| Mix 5 | acetyl-L-carnitine, alpha-lipoic acid, vitamins, cardiolipin, antioxidants |

TABLE 2-continued

| mixture | Components[1] |
|---------|---------------|
| Mix 6 | acetyl-L-carnitine, alpha-lipoic acid, antioxidants, biotin |
| Mix 7 | biotin, acetyl-L-carnitine, alpha-lipoic acid, calcium, choline, cardiolipin |
| Mix 8 | biotin, acetyl-L-carnitine, alpha-lipoic acid, calcium, choline, cardiolipin, vitamins |
| Mix 9 | biotin, acetyl-L-carnitine, alpha-lipoic acid, calcium, choline, cardiolipin, antioxidants |
| Mix 10 | All components of mixtures 1-9 |
| Mix 11 | omega 3 and 6 fatty acids, vitamins |
| Mix 12 | omega3 and 6 fatty acids, antioxidants |
| Mix 13 | biotin, acetyl-L-carnitine, alpha-lipoic acid, calcium, omega3 and 6 fatty acids, cardiolipin, choline |

[1]Where the table refers generically to "antioxidant" or "vitamin" the antioxidant or vitamin can be selected from any described herein, respectively.

Cell Culture Models

A. Normal Fibroblasts Exposed to Mitochondrial Toxins

To inhibit complex I mitochondrial enzymes, normal human skin fibroblasts can be grown under standard conditions and treated with increasing concentrations of rotenone. To inhibit all mtDNA encoded mitochondrial enzymes of the electron transport chain (ETC), cells can be exposed to ethidium bromide (Li et al., *J Biol. Chem.* 278:8516 (2003); Miller et al., *J Neurochem.* 67:1897 (1996); and Panov et al., *J Biol. Chem.* 280:42026 (2005)). Following treatments, cell homogenates and media as well as purified mitochondria can be collected and evaluated by functional assays as described above. Sister cultures treated in a similar fashion and can be processed for light and electron microscopy using the probes mentioned. Fibroblasts grown in the same medium without rotenone or ethidium bromide can be used throughout as controls.

B. Fibroblasts from Patients with BD

Figure 2:
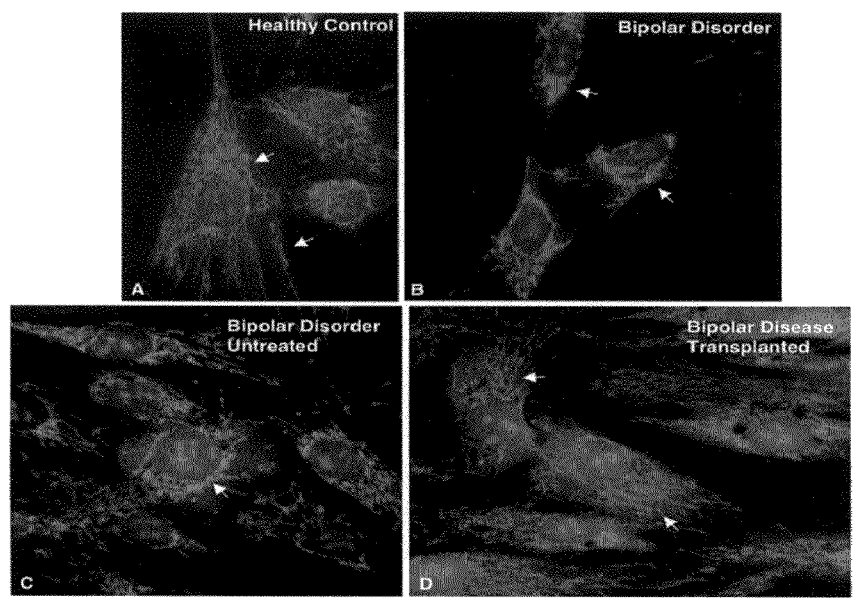
FIG. 2 is a photograph showing that fibroblasts from patients with bipolar disorder exhibit abnormalities in mitochondrial structure (see FIG. 2a vs.
Figure 4:
FIG. 4 is a photograph depicting (FIG. 4a) brain distribution in adult mouse brain of liposome packaged mitochondria following intravenous administration.
Figure 4:
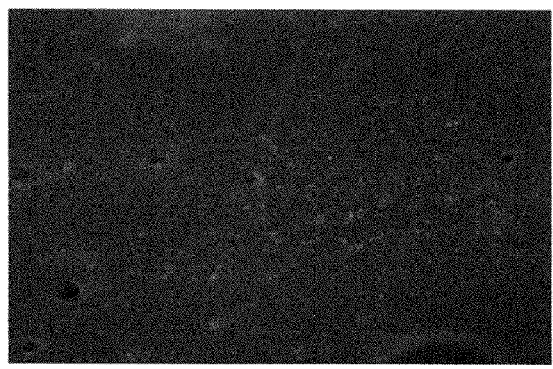

Our studies show that fibroblasts from patients with BD exhibit abnormalities in mitochondrial structure (FIG. 2, A vs. B). In addition, we have found that transplantation of healthy mitochondria to BD fibroblasts restores the normal mitochondrial phenotype (FIG. 2, C vs D).

C. MtDNA-Depleted Neuronal Cell Line

A respiratory deficient neuroblastoma cell line can be generated as described by (Chomyn, *Methods Enzymol* 264:334 (1996); Miller et al., *J Neurochem.* 67:1897 (1996); King et al., *Cell* 52:811 (1988); and King et al., *Science* 246:500 (1989)) by selectively depleting mtDNA through prolonged exposure to ethidium bromide. Differentiation can be induced for 2 to 3 weeks using retinoic acid.

Animal Models

The methods, kits, and compositions of the invention can be used to rescue cells having impaired function associated with mitochondrial dysfunction as demonstrated in the bitransgenic mouse and POLG transgenic mouse models described below.

A. Bitransgenic Mice

Mice expressing a tetracycline-controlled transactivator driven by human glial fibrillary acidic protein (GFAP) promoter can be mated with a second transgenic strain which carries a gene(s) of interest under the regulation of the tetracycline-responsive promoter. Expression of the gene of interest in the bitransgenic offspring can be induced in astrocytes by withdrawal of the tetracycline analog, doxycycline, administered in drinking water. Defective oxidative phosphorylation in astrocytes can be induced by expression of genetic variations of complex I enzymes and a targeted mutant of cytochrome C. Non-transgenic littermates can be used as controls. Following the administration of standard behavioral testing, tissue blocks of the frontal lobe, hippocampus, basal ganglia and cerebellum can be harvested for morphological and structural analyses.

B. POLG Transgenic Mice

Transgenic (tg) mice with a neuron-specific defect in the POLG gene, which encodes for nuclear-encoded mtDNA polymerase, can be obtained from Jackson Laboratories. These animals exhibit forebrain specific defects in mtDNA and behavioral characteristics resembling mood disorders, such as BD. Mice ranging in age from 17 weeks to 12 months that display progressive phenotypic changes (Kasahara et al., *Molecular Psychiatry* 11:577 (2006)) can be examined. Non-tg mice can be used as controls. Because of the synergy between neurons and glia, mutations in POLG that affect mtDNA replication or ETC enzymes in neurons could potentially alter energy-dependent interactions between glia and neurons and thereby alter glial energy metabolism and viability.

Example 2

Diagnoses Based Upon Abnormalities in Mitochondrial Structure

Mitochondria in Neurons of BD Brain are Abnormal in Shape

Figure 5:
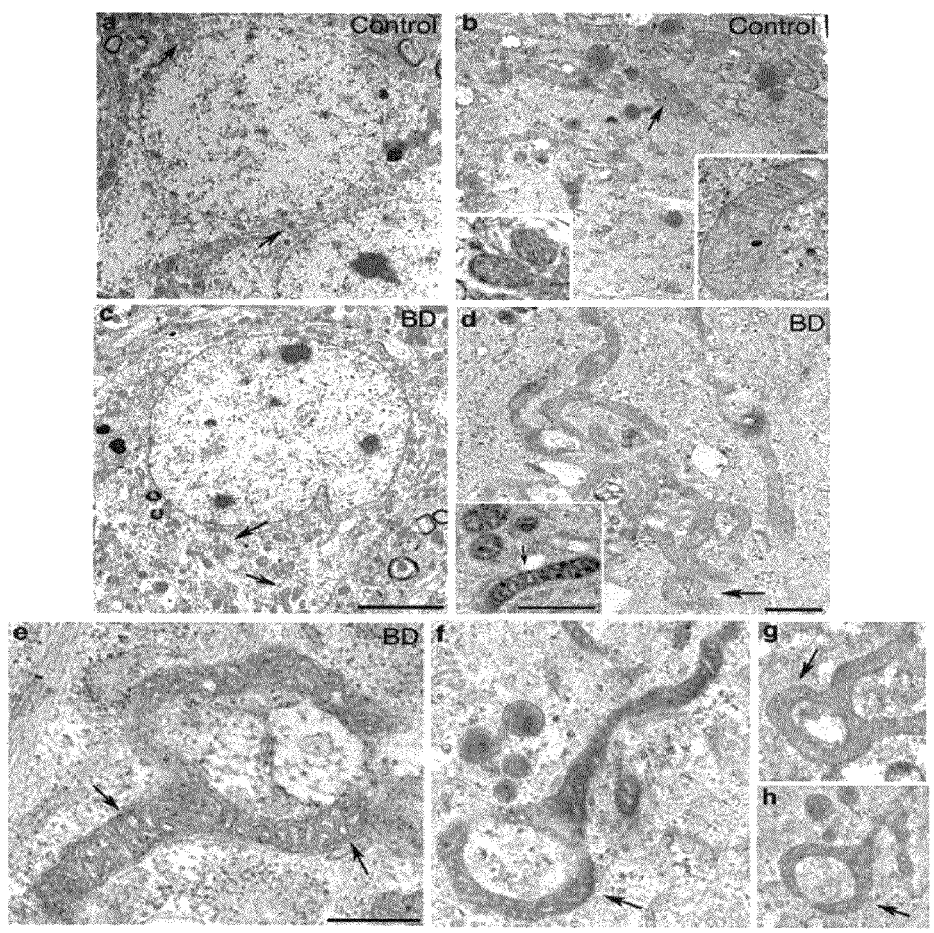
FIG. 5 is a photograph showing that neurons of patients with BD display alterations in mitochondrial shape. Representative ultrastructural images of the prefrontal cortex show the atypical mitochondrial morphology and distribution (FIG. 5c-h) in neurons from patients with BD compared to those from age-matched controls (FIGS. 5a and b). In brains from patients with BD, many mitochondria appeared as cup-shaped or circular profiles (FIGS. 5d and f-h, arrows) with distended intercristae spaces (FIG. 5d inset and 5e, arrows) compared to mitochondria in healthy controls (FIG. 5b insets). The low magnification images in FIGS. 5a and 5c highlight the perinuclear clustering of mitochondria in the BD patients (FIG. 5c, arrows) in contrast to the dispersed mitochondrial profiles in control patients (FIG. 5a, arrows).

We initially sought to determine if changes in mitochondrial morphology and spatial distribution were present in the prefrontal cortex of postmortem brain from patients diagnosed in life with BD. Prefrontal cortex was chosen as it is a documented site of abnormalities in brain structure and function in patients with BD (Ongur et al., *Proc. Natl. Acad. Sci.* 95:13290-13295 (1998)). Ultrastructural examination of human brain tissue from healthy controls showed, in both neurons and glia, that mitochondrial profiles were distributed randomly throughout the cell soma in close proximity to the nucleus (FIG. 5a) as well as more peripherally within processes (data not shown). Most mitochondria appeared as small rounded structures approximately 0.5 μm in width or as rod-shaped profiles 0.1 μM in diameter and several microns in length. Each organelle was bounded by a smooth outer membrane and had invaginated inner cristae. Branching was not uncommon and, frequently, small mitochondria profiles were seen interspersed with several larger profiles (FIG. 5a,b).

In sections of brains from patients with BD, the distribution and morphology of mitochondria were dramatically different. In the cell body, mitochondrial profiles aggregated in the perinuclear region (FIG. 5c,d) and the extent of the clustering varied from cell to cell. Mitochondrial profiles varied in size but, compared to those from healthy brain, most profiles were longer and exhibited few branches. Higher magnification images of these profiles (FIG. 5d,e) revealed that they were condensed with large intercristae spaces and narrow junctions between cristae. A number of mitochondria in tissue from patients with BD also appeared cup- or ringed shaped (FIG. 5d-h).

BD Fibroblasts and Lymphocytes Exhibit Alterations in Mitochondrial Morphology

Figure 6:
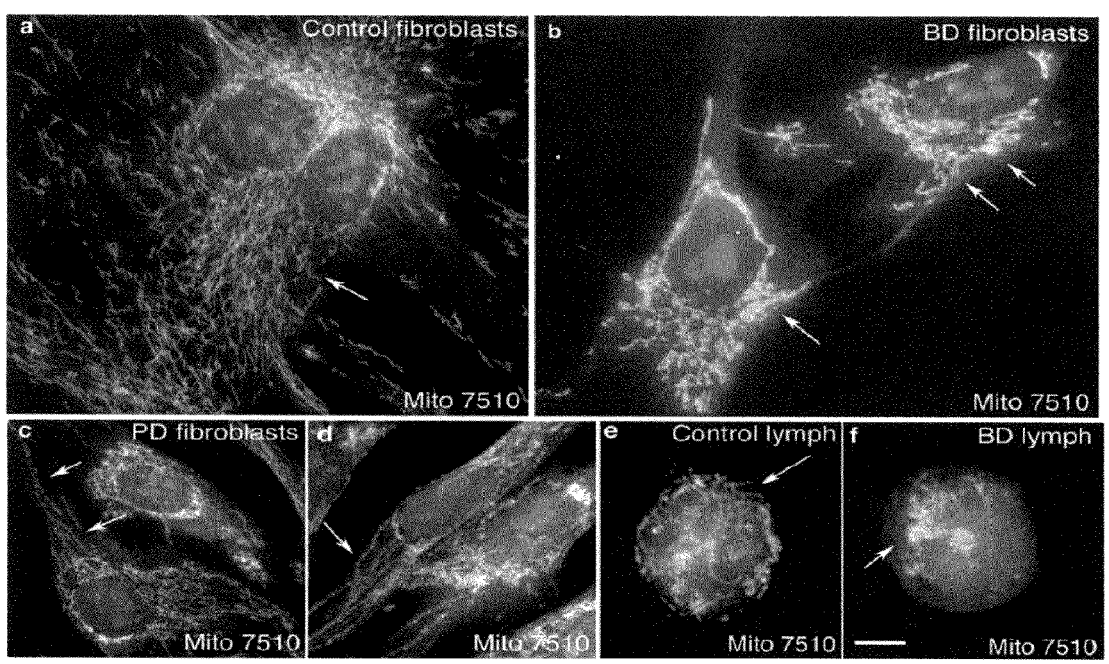
FIG. 6 is a photograph showing mitochondrial clustering in primary cells from patients with BD. Compared to control cells, (FIGS. 6a and e, arrows), mitochondrial morphology and distribution were dramatically altered in primary fibroblasts (FIG. 6b, arrows) and lymphocytes (FIG. 6f, arrow) from patients with BD. In the majority (greater than 90%) of these cells, perinuclear clusters revealed using Mitotracker 7510 fluorescence, were observed. The clusters varied in size and were often composed of ring-shaped or circular mitochondrial profiles. Fibroblasts from patients with PD (FIGS. 6c and d) with known mitochondrial DNA defects, display mitochondrial fragmentation (arrows) but do not exhibit the extensive clustering seen in cells from the BD patients. Panels 6a-f, bar=10 µm.

While alterations in mitochondrial morphology in postmortem brain are suggestive of altered mitochondrial function in BD, demonstrating a disease-specific relationship between mitochondrial morphology and altered mitochondrial and energy metabolism requires living human tissue. Given that brain showed morphological alterations in mitochondrial shape and distribution, we next determined if, like brain, primary non-neuronal cells—fibroblasts and lymphocytes harvested antemortem from individuals with BD—would show mitochondrial abnormalities. We used the mitochondrial—selective fluorescent marker M7510 to identify mitochondria and to examine mitochondrial structure and organization. Labeling of fibroblasts (FIG. 6a) and lymphocytes (FIG. 6e) from healthy control subjects revealed a predominantly dispersed network of elongated and branched mitochondria which showed connectivity and varying degrees of fusion. The mitochondria were typically organized around the nucleus with longer tubular networks that extended to the plasma membrane. In comparison to all control fibroblasts and lymphocyte lines examined, mitochondrial structure revealed by Mitotracker 7510 staining in the BD cell lines was dramatically altered (FIG. 6b,f). The mitochondrial morphology in most cells from patients with BD showed extensive perinuclear clustering, which was seen in greater than 90% of the cells. Within the clusters, mitochondria frequently appeared as punctate, cup- or ring-shaped fluorescent profiles with little branching—a finding that was observed in both lymphocytes and fibroblast cell lines regardless of the age of the individual. The clusters varied in size but were substantially larger than those in control cells. In some BD cells, long mitochondrial profiles were retained but were fewer in number than those in control cells and were present in the same cells displaying large mitochondrial clusters.

Given that genetic studies have implicated abnormalities in mitochondrial DNA and function in the pathogenesis of Parkinson's disease (PD; see e.g., Beal, *Free Rad. Biol.* 32:797-803 (2002), Beal, *Ann. Neurol.* 58:495-505 (2005), and Fahn et al., *NeuroRx.* 1:139-154 (2004)), we examined fibroblasts from patients with PD to determine if these cells displayed alterations in mitochondrial structure similar to those seen in BD. Mitochondrial profiles in fibroblasts from patients with PD (FIG. 6c,d) labeled with Mitotraker 7510 showed a dispersed mitochondrial distribution similar to that seen in fibroblasts from healthy control subjects. Unlike the healthy controls and subjects with BD, fibroblasts from individuals with PD exhibited a large degree of mitochondrial fragmentation.

Figure 7:
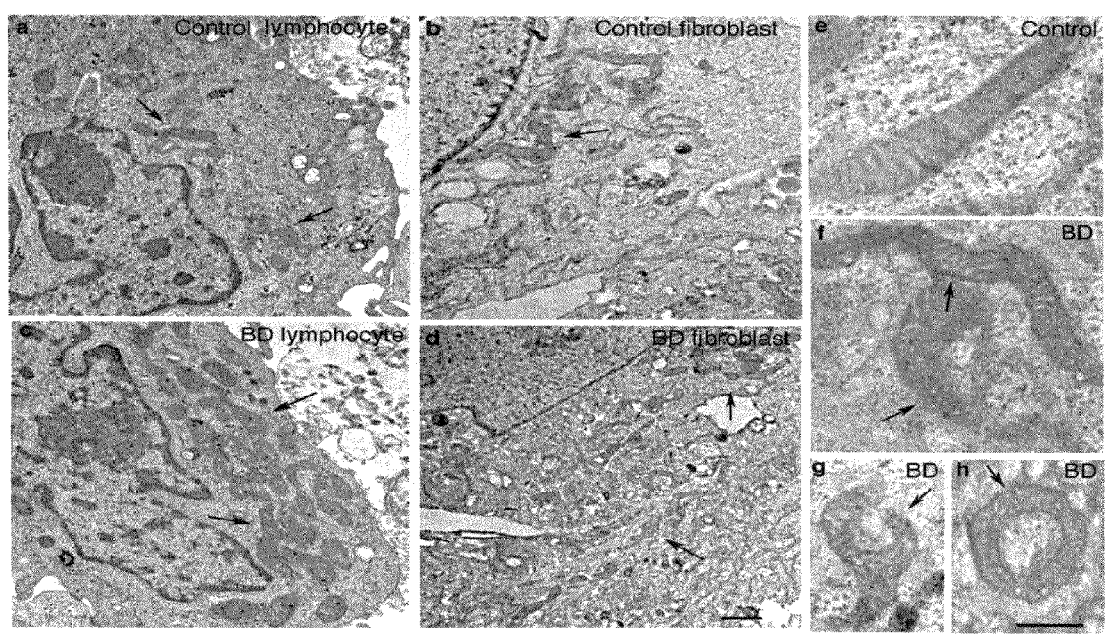
FIG. 7 is a photograph showing ultrastructural alterations in mitochondrial morphology in peripheral cells from patients with BD. By EM, mitochondria in lymphocytes and fibroblasts from healthy control subjects (FIGS. 7a and b, arrows) were distributed randomly throughout the cytoplasm. By comparison, lymphocytes and fibroblasts from patients with BD (FIGS. 7c and d, arrows) showed mitochondria collapsed and clustered close to the nucleus—consistent with the light microscopic findings (compare with FIGS. 6b and f). Mitochondrial profiles in these cells showed little evidence of branching. As in neurons, mitochondrial profiles in cultured cells from the subjects with BD were predominantly arranged in perinuclear clusters, in contrast to the dispersed mitochondrial network in cells from healthy subjects and were often ring-, or cup-shaped, or, less frequently, circular (FIGS. 7g and h, arrows). Cristae were swollen or ill-defined (FIG. 7f-h, arrows) compared to healthy controls (FIG. 7e).

We used electron microscopy to further examine the subcellular features of mitochondria in BD and control cell lines. In fibroblasts and lymphocytes from healthy control subjects (FIG. 7a,c,e) the mitochondria were distributed randomly throughout the cytoplasm. By comparison, fibroblasts and lymphocytes from patients with BD showed collapsed mitochondria, which were clustered close to the nucleus (FIGS. 7b and d)—consistent with the light microscopic findings. Mitochondrial profiles in these cells showed little evidence of branching. As in neurons, mitochondrial profiles in cultured cells from the subjects with BD were predominantly arranged in perinuclear clusters, in contrast to the dispersed mitochondrial network in cells from healthy subjects (FIG. 7a,b.; see also FIG. 6a,e), and were often ring or cup-shaped, or, less frequently, circular (FIG. 7g,h). Cristae were swollen or ill-defined (FIG. 7d,f). In contrast to the altered structure and cellular arrangement of the mitochondria in the BD cells, other organelles such as the plasma membrane, ER, and Golgi apparatus appeared similar to those in control cells.

Figure 8:
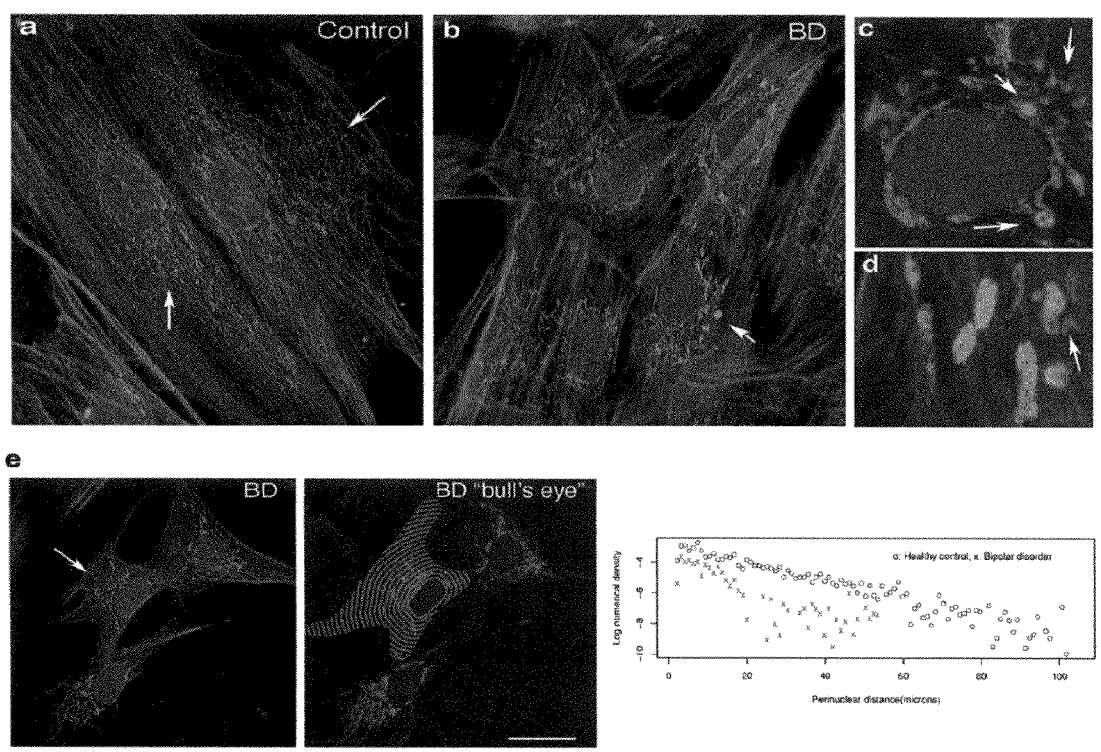
FIG. 8 is a photograph showing mitochondrial distribution in fibroblasts from control and BD individuals. Representative images of fibroblasts from patients with BD (FIG. 8b) and control (FIG. 8a) labeled with probes for mitochondria (green, Mitotracker 7510) and filamentous actin (red, phalloidin) show the dramatic mitochondrial redistribution and perinuclear clustering in the BD fibroblasts compared with controls. We found that in cells from BD individuals (FIG. 8b-d), abnormalities in mitochondrial shape (arrows) and distribution were not accompanied by cytoskeleton changes when compared to healthy controls (FIG. 8a). In addition, fluorescent staining of fibroblasts with the DNA-binding dyes, DAPI or bisbenzimide (blue label), revealed no evidence of apoptosis or nuclear fragmentation in the BD cells.

Fibroblasts from Patients with BD do not Exhibit Cytoskeletal Alterations or Apoptosis Using F-actin selective phalloidin (red label, FIG. 8a,b) or actin immunocytochemistry (data not shown), we found that abnormalities in mitochondrial shape and distribution (green label, FIG. 8b-d) were not accompanied by cytoskeleton changes in cells from BD individuals (FIG. 8b), which showed a cytoskeletal pattern similar to that seen in healthy controls (FIG. 8a). In addition, fluorescent staining of fibroblasts with the DNA-binding dyes DAPI or bisbenzimide (blue label), revealed no evidence of apoptosis or nuclear fragmentation in the BD cells (FIG. 8b) compared with controls (FIG. 8a).

Redistribution of Mitochondria in Primary Cells from BD Patients

As validation of the dramatic perinuclear accumulation of mitochondria revealed by morphological examination of the BD cells, we examined spatial variation in the perinuclear distribution of mitochondria in nine fibroblasts from each of n=6 subjects with BD (total BD cells analyzed=54) and in five fibroblasts from each of n=6 healthy age-matched control subjects (total healthy cells analyzed=35). Each subject contributed one digital image of a randomly placed field of view; the number of cells/image varied from 1 to 7 across subjects, with larger numbers of cells/image in random fields from BD subjects. We observed that relative to the healthy controls, fibroblasts from individuals with BD appeared to possess higher mitochondrial densities as a function of radial distance from the nuclear envelope (FIG. 8e, left). We then applied our segmentation algorithm to measure numerical density objectively (FIG. 8e, center). Resultant data for a cell from a BD subject (red) and a healthy control subject (blue) are displayed in FIG. 8e, right. Our ANCOVA model confirmed that average mitochondrial density for healthy subjects declined by −0.0004/micron (SE=0.0001, ANCOVA t-value −9.02, $p<5\times10^{-4}$) from the nuclear envelope but was constant for the BD subjects on average and with higher variability. Specifically, the BD group exhibited significantly less decline in numerical densities at perinuclear distances proximal to the nuclear envelope than those seen in healthy subjects (SE=0.0002, ANCOVA t-value 2.62, p=0.008).

Lithium Effects on Mitochondrial Structure

Mood stabilizing drugs like lithium are commonly used as treatment for BD (Friedman et al., *Biol. Psychiatr.* 56:340-348 (2004) and Goodwin et al., *JAMA* 290:1467-1473 (2003)), and all but one of our subjects with BD was receiving lithium. Therefore, we next determined whether lithium treatment could promote changes in mitochondrial structure similar to those seen in fibroblasts or lymphocytes from BD patients. Control fibroblasts and lymphocytes were treated with 2 mM lithium carbonate ($LiCO_3$; approximately twice the average serum level of lithium in patients) for 3 and 5 days. Cells treated with a water vehicle only served as controls. Light microscopic examination using the fluorescent mitochondrial marker, 7510, revealed no significant differences in mitochondrial shape and distribution in cell lines exposed to $LiCO_3$ compared to vehicle treated cells (data not shown).

Impaired Mitochondrial Function with Metabolic Stress in BD Fibroblasts

Figure 9:
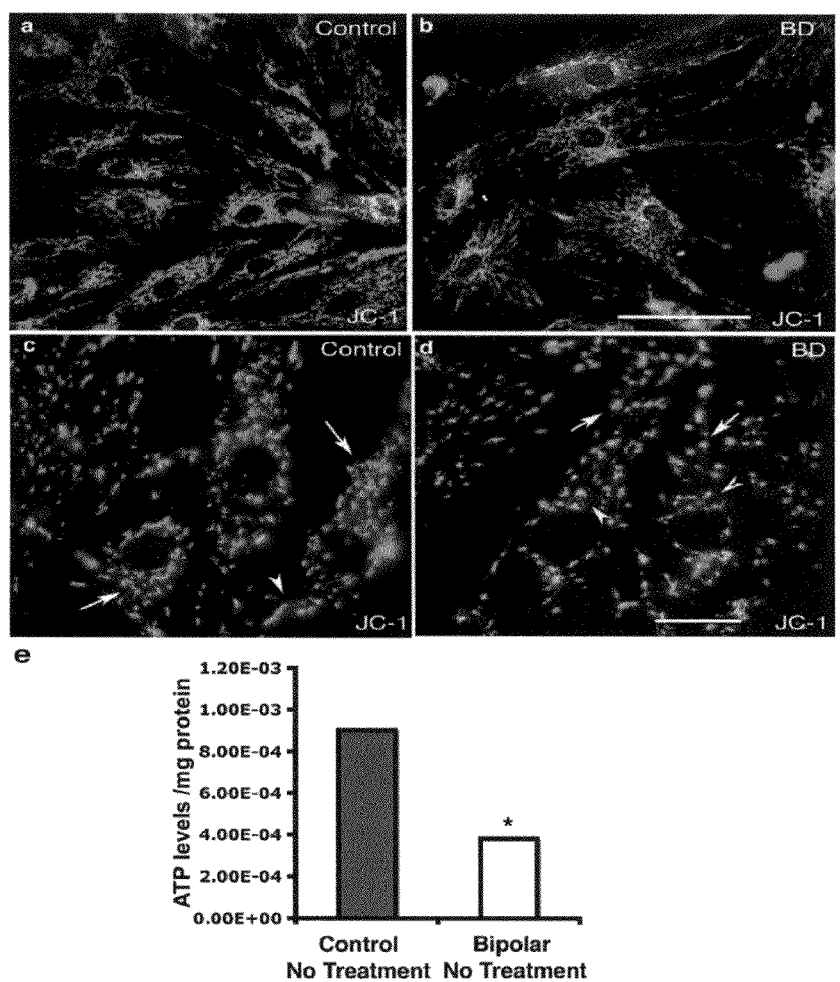
FIG. 9 is a photograph showing the loss of mitochondrial function in fibroblasts from patients with BD. Staining of live, unfixed fibroblasts with JC-1 revealed loss of the red J-aggregate fluorescence and the cytoplasmic diffusion of the green monomeric fluorescence in individuals with BD (FIGS. 9b and d) indicating collapse of mitochondrial membrane potential compared with normal controls (FIGS. 9a and c). Higher magnification photomicrographs of cells from controls (FIG. 9c) and BD individuals (FIG. 9d) visualized by fluorescence microscopy show regions of high mitochondrial polarization due to red aggregate fluorescence by the concentrated dye (arrows). Depolarized regions of the mitochondrial membrane are indicated by the green fluorescence of the JC-1 monomers (FIGS. 9c and d, arrowheads).

To determine whether the abnormal mitochondrial morphology we observed in neurons and primary cultured cells from patients with BD was predictive of hormonal or oxidative stress-induced functional changes in the mitochondria, we measured two stress parameters: (1) ATP levels, using a biochemical luciferase-based assay, and (2) morphological changes in mitochondrial membrane potential using the cationic fluorescent dye, JC-1, in untreated fibroblasts and in fibroblast lines exposed to either hydrocortisone or hydrogen peroxide challenge. Loss of red JC1 signal relative to monomeric green JC1 indicates collapse of mitochondrial membrane permeability (Smiley et al., *Proc. Natl. Acad. Sci.* 88:3671-3675 (1991) and Cossarizza et al., *Biochem. Biophys. Res. Comm.* 197:40-45 (1993)). Under basal metabolic conditions, healthy fibroblasts stained with JC1 displayed numerous dense red fluorescent aggregates, consistent with efficient mitochondria and intact mitochondrial membrane potential (FIG. 9a,c). The green fluorescent monomeric from of JC1 was also present in the cytosol of control cells but in low levels (FIG. 9a,c). In contrast to the control fibroblasts, BD fibroblasts exhibited fewer detectable red fluorescent mitochondrial aggregates of JC1 (FIG. 8b,d) and elevated levels of green fluorescent monomeric JC1 in the cytoplasm (FIG. 9b,d). Quantitative analyses of JC-1 monomers and aggregates showed differences in the ratio of red to green fluorescence which did not reach statistical significance. However, the determination of ATP levels using bioluminescence, revealed a 2.4-fold decrease in the levels of ATP in fibroblasts from subjects with BD from patients compared to control fibroblasts (FIG. 8e; Control fibroblasts, no treatment—mean=$9.02\times10^{-4}$, SE $2.3\times10^{-4}$; BD fibroblasts, no treatment—mean=$3.8\times10^{-4}$, SE $5.4\times10^{-5}$; p<0.05).

Figure 10:
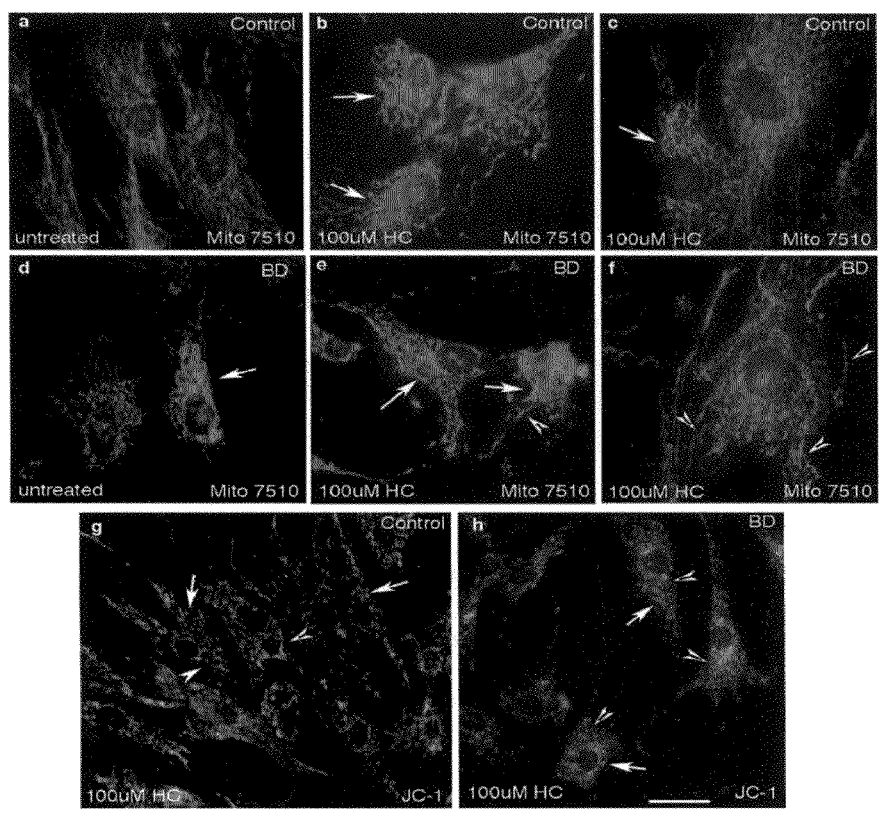
FIG. 10 is a photograph showing alterations in mitochondrial function coincide with abnormal mitochondrial shape following treatment with hydrocortisone. Following 24 hr treatment with 100 µM HC, mitochondria in control fibroblasts visualized with MitoTracker 7510 showed a slight loss in the reticular pattern of the mitochondrial network and greater frequency of perinuclear clustering (FIGS. 10b and c, arrows) compared to untreated cells (FIG. 10a). Mitochondria from BD subjects labeled with MitoTracker 7510 and exposed to the same concentration of HC (FIGS. 10e and f) displayed perinuclear clustering (arrows) like that seen in untreated cells (10d, arrow) but a greater degree of mitochondrial fragmentation (arrowheads). JC-1 staining of fibroblasts from healthy individuals treated with HC (FIG. 10g) revealed loss of red mitochondrial aggregates (arrows) in most cells with an increase in the green JC1 monomeric form (arrowheads) compared to untreated cells (compare with FIGS. 9a and c). JC1 staining of BD fibroblasts treated with HC (FIG. 10h) revealed a loss of red JC1 mitochondrial aggregates in the majority of cells as well as a qualitative increase in JC1 monomeric green fluorescence (arrowheads) than that seen in untreated fibroblasts from these patients (compare with FIGS. 9a and c).

Using the same techniques, we examined the role of stress-related responses to mitochondrial dysfunction and energy metabolism in BD. Following 24 hr treatment with 100 μM hydrocortisone (HC), light microscopic examination of mitochondria in control fibroblasts visualized with MitoTracker 7510 showed some loss in the reticular pattern of mitochondria (FIG. 10b,c) in treated compared to untreated cells (FIG. 10a). JC-1 staining of fibroblasts from healthy individuals treated with HC (FIG. 10g) revealed loss of red mitochondrial aggregates in most cells with detectable increases in the green JC1 monomeric form compared to untreated cells (compare with FIGS. 9a and c). Mitochondria from BD subjects labeled with MitoTracker 7510 and exposed to the same concentration of HC (FIG. 10e,f) displayed perinuclear clustering like that seen in untreated cells but a greater degree of mitochondrial fragmentation compared to treated control cells (FIG. 10b,c). JC1 staining of BD fibroblasts treated with HC (FIG. 10h) revealed an even greater loss of red JC1 mitochondrial aggregates as well as a qualitative increase in JC1 monomeric green fluorescence. Despite the qualitative differences in JC1 signal seen by fluorescence microscopy, ratiometric changes in JC1 and differences in ATP levels after treatment did not reach statistical significance (data not shown).

Figure 11:
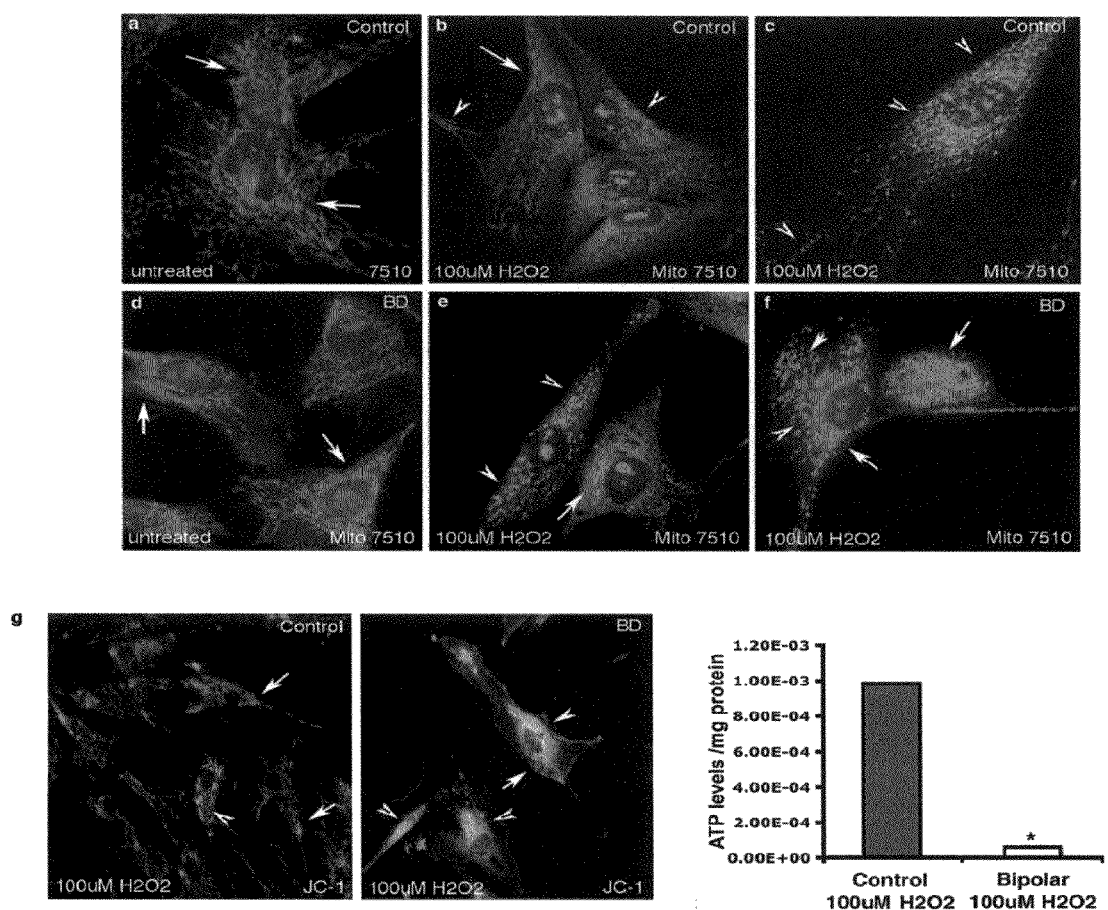
FIG. 11 is a photograph showing that exposure to $H_2O_2$ stress exacerbates mitochondrial dysfunction in fibroblasts from BD patients. Following exposure with $H_2O_2$ (FIGS. 11b and c), control fibroblasts stained with Mitotracker 7510 displayed dispersion of the mitochondrial network with loss of elongated mitochondrial profiles, increased perinuclear clustering (arrows), and increased mitochondrial fragmentation (arrowheads) compared to untreated cells (FIG. 11a, arrows). Disturbances in mitochondrial structure and function were enhanced in fibroblasts from patients with BD following oxidative stress induced with $H_2O_2$. Fibroblasts from BD patients labeled with MitoTracker 7510 (FIG. 11e and f) showed almost complete loss of the mitochondrial network, mitochondrial clustering and dramatic mitochondrial fragmentation (arrows) compared to untreated cells (arrows). In healthy control cells exposed to $H_2O_2$, the alterations in mitochondrial morphology were accompanied by loss of mitochondrial permeability, revealed by reduced JC1 red aggregates (arrows) and increased JC1 cytosolic monomeric staining (arrowheads) (FIG. 11g, left panel). ATP levels measured by bioluminescence assay showed no significant difference in ATP compared to untreated control cells. In fibroblasts from patients with BD exposed to $H_2O_2$, JC1 staining revealed severe loss of mitochondrial membrane integrity that correlated with little to no JC1 red aggregate staining (arrows) and high levels of monomeric JC1 (green) in the cytoplasm (arrowheads) (FIG. 11g, middle panel). The morphologic alterations in mitochondrial membrane potential seen with JC1 staining—a change consistent with collapse of the mitochondrial electrochemical gradient were accompanied by a 83% decrease in ATP levels in fibroblasts from BD subjects exposed to $H_2O_2$ compared to untreated fibroblasts (BD fibroblasts, no treatment—mean=$3.8\times10^{-4}$, SE $5.4\times10^{-5}$; BD fibroblasts, $H_2O_2$ treated—mean=$6.2\times10^{-5}$, SE $4.2\times10^{-5}$, p<0.001) and a 93% decrease compared to control cells exposed to $H_2O_2$ (control fibroblasts, $H_2O_2$ treated—mean=$9.9\times10^{-4}$, SE $4.3\times10^{-4}$; BD fibroblasts, $H_2O_2$ treated—mean=$6.2\times10^{-4}$, SE $4.2\times10^{-5}$, p<0.05).

We next examined whether increased oxidative stress would exacerbate mitochondrial energy dysfunction in BD. Control fibroblasts treated with 100 μm $H_2O_2$ for 24 hrs exhibited dramatic changes in mitochondrial structure. Mitochondria in cells exposed to $H_2O_2$ and labeled with MitoTracker 7510 (FIG. 11b,c) showed a dispersed mitochondrial network with loss of elongated mitochondrial profiles, increased perinuclear clustering, and increased mitochondrial fragmentation compared to untreated cells (FIG. 11a). These alterations in mitochondrial morphology also were accompanied by loss of mitochondrial permeability, revealed by reduced JC1 red aggregates and increased JC1 cytosolic monomeric staining (FIG. 11g, left panel). ATP levels measured by bioluminescence assay showed no significant difference in ATP compared to untreated control cells. Disturbances in mitochondrial structure and function were enhanced in fibroblasts from patients with BD following oxidative stress induced with $H_2O_2$. Fibroblasts from BD patients labeled with MitoTracker 7510 (FIG. 11 e,f) showed almost complete loss of the mitochondrial network, mitochondrial clustering and dramatic mitochondrial fragmentation (FIG. 11e,f) compared to untreated cells (FIG. 11d). JC1 staining revealed severe loss of mitochondrial membrane integrity that correlated with little to no JC1 red aggregate staining and high levels of monomeric JC1 (green) in the cytoplasm (FIG. 11g, middle panel). The morphologic alterations in mitochondrial membrane potential seen with JC1 staining—a change consistent with collapse of the mitochondrial electrochemical gradient—were accompanied by a 83% decrease in ATP levels in fibroblasts from BD subjects exposed to $H_2O_2$ compared to untreated fibroblasts (BD fibroblasts, no treatment—mean=$3.8\times10^{-4}$, SE $5.4\times10^{-5}$; BD fibroblasts, $H_2O_2$ treated—mean=$6.2\times10^{-5}$, SE $4.2\times10^{-5}$, $p<0.001$) and a 93% decrease compared to control cells exposed to $H_2O_2$ (Control fibroblasts, $H_2O_2$ treated—mean=$9.9\times10^{-4}$, SE $4.3\times10^{-4}$; BD fibroblasts, $H_2O_2$ treated—mean=$6.2\times10^{-4}$, SE $4.2\times10^{-5}$, $p<0.05$).

Methods

Human Brain Tissue

Postmortem brain tissue five individuals ranging in age from 61-74 years diagnosed with manic-depressive Bipolar Disorder, Type 1 according to the guidelines of DSM IV (REFS) were used in this study. We also studied an equal number of age-matched individuals ranging in age from 51-78 with no known history of psychiatric illness who were evaluated using the same criteria. In addition, brain tissue from five cases with Parkinson's Disease (PD) and five age-matched controls were examined. The PD and control group ranged in age from 68-84 years and neither group presented with clinical symptoms consistent with BD. Fixed BD, control and PD tissue were obtained from the Harvard Brain Tissue Resource Center at McLean Hospital Belmont, Mass.).

Cells

All primary human skin fibroblasts and lymphocyte lines were obtained from Coriell Institute of Medical Research, Camden N.J. A total of 12 fibroblast lines (n=6 Bipolar Disorder—BD; n=6 age-matched normal controls) and 12 lymphocyte lines (n=6 BD; n=6 controls) ranging in age from 20 yrs to 65 yrs old were used for the study. The diagnosis of BD (guidelines established in DSM IV) along with medication status of the subjects was documented for each line. In addition, a second group of human fibroblasts from four individuals with PD were purchased from Coriell Institute. Age-matched control cell lines were obtained from individuals with no history of psychiatric illness.

Cell Culture

Fibroblast cell lines were grown in Minimal Essential Media plus 15% fetal bovine serum and 1% glutamine, penicillin streptomycin in 5% $CO_2$. Lymphocytes were grown in RPMI plus 15% FBS and 1% glutamine, penicillin streptomycin in 5% $CO_2$. All cell culture media was from Invitrogen. Media was changed every other day. Cell lines were used between passages 3 and 14.

Mitochondrial Probes

The fluorescent marker, MitoTracker-M7510 (Invitrogen, Carlsbad Calif.), was used to visualize mitochondria according to manufacturers instructions. Briefly, fibroblasts were plated at $2.5\times10^4$ and grown on coverslips, subsequently washed one time with pre-warmed growth media and incubated with M7510 at a final concentration of 250 nM in culture media at 37° C., 5% $CO_2$ for 30 min. Cells were then washed once with culture media and fixed in 4% paraformaldehyde in 100 mM phosphate buffer pH 7.4 for 15 min. Following fixation, coverslips were rinsed two times in PBS and mounted in Gel Mount (Biomedia).

Microscopic Analysis of Mitochondrial Membrane Potential

The cationic fluorescent dye, JC-1 (5,5',6,6'-tetrachloro-1,1',3,3'-tetraethylbenzimidazolylcarbocyanine iodide) (Strategene, La Jolla, Calif. USA), was used to detect changes in mitochondrial membrane potential according to manufacturer's protocol. JC-1 reagent produces a red fluorescence (absorption/emission maxima=585/590 nm) after accumulation and aggregation in healthy, non-apoptotic cells with intact mitochondrial membrane potential and localizes to the cytoplasm as green with JC-1 monomers fluorescence (absorption/emission maxima=510/527 nm) in cells with compromised membrane potential. Briefly, cell lines were plated at a concentration of $2.5\times10^4$ oncoverslips and were incubated with a 1:100 dilution of pre-warmed JC1 in growth media for 15 to 20 min at 37° C., 5% $CO_2$. Cells were then rinsed once with assay buffer and mounted in PBS and analyzed immediately on a fluorescence microscopy. The coverslips were placed on standard microscopy slides and viewed immediately using a Zeiss Axiskop 2 epifluorescence microscope.

Immunocytochemistry

Cultures grown on glass coverslips were generated for analyses by immunolabeling. Cells on coverslips were washed three times with PBS and fixed for 20 min at room temperature with 4% paraformaldehyde, processed for immunofluorescent labeling with actin (Sigma-Aldrich Corp., St. Louis, Mo.) as previously described (REFS). Briefly, cells were then rinsed three times in PBS following fixation with aldehydes and blocked for 30 min. Fibroblasts were incubated in primary antibody overnight at room temperature with gentle rocking. Cells were then washed three times with diluting buffer followed by incubation in fluorescent-conjugated secondary antibodies for 2 to 3 hrs at room temperature. Coverslips were mounted and examined using a Zeiss epifluorescent microscope. In some experiments, cytoskeletal integrity was examined using phalloidin 568 was added to the secondary antibody at a dilution of 1:200 for an additional 30 min. Cells were then washed 2 times with PBS and mounted in gel mount that contained either 4',6-diamidino-2-phenylindole (DAPI) at a final concentration of $1\times10^4$ or bisbenzimide (Hoechst 33258) (5 μg/ml) for visualization of nuclear changes indicative of apoptotis.

Determination of ATP Levels

ATP production was measured in cultured fibroblast lines using the Roche ATP Bioluminescence assay kit CLSII following the manufacturer's protocol (Roche Diagnostics, Mannheim, Germany). Briefly, cells were plated at a concentration of $2.5\times10^5$ cells per 60 mm dish were used for each experiment and experiments were conducted two days later. Cell lysis was achieved by boiling in lysis solution (100 nM Tris, 4 mM EDTA, pH=7.75) followed by incubation for 2 min at 100° C. The cells then were centrifuges spun at 1000×g for 1 min. The supernatants were used for total cell ATP determination. Samples were run in triplicate on a 96-well plate MLX luminometer (Dynex Technologies, Chantilly, Va., USA). Integration was delayed for 1 sec after the addition of luciferase and luminescence was measured for 10 seconds at an emission maximum of 562 nM. Following ATP luminescence measurements, data was normalized to protein concentration as determined by the method of Bradford (Bradford DC assay, BioRad, Temecula, Calif., USA) to yield nanograms of ATP per mg of protein. Assays were performed in triplicate.

Statistical Analysis of Mitochondrial Distribution Using Digital Images

For each cell in each digital image, we traced inner and outer cellular boundaries manually. The inner cellular boundary was defined to coincide with the nuclear envelope and the outer boundary was defined to contain all mitochondria within the spatial extent of the fibers surrounding the nucleus. No overlap was allowed between outer boundaries for different cells. For each cell, a set of concentric, equally-spaced scaled copies of the inner boundary was placed at the nuclear centroid to define expanding annuli that covered the entire irregularly shaped space between inner and outer boundaries. We then employed a segmentation algorithm (Young et al., *Biostatistics* 2:351-364 (2001)) to quantify mitochondria within each annulus. As a potential discriminator between bipolar and healthy cells, we defined mitochondrial numerical density within each annulus as the ratio of the sum of the areas of mitochondrial clusters to total annular area (Weibel, "Stereological Methods," Vol. 2. Theoretical Fundations. Academic Press, London (1980) and Baddeley et al., "Stereology for statisticians," Chapman & Hall/CRC (2005)). We employed a mixed effects analysis of covariance model for formal statistical analysis. Our model included an overall intercept term, a BD versus healthy control grouping factor, perinuclear distance and a group by distance interaction. Cells were treated as nested within images that were nested within subjects and numerical density was re-expressed on the logarithmic scale to conform to the constant variance and Gaussian distribution properties of the general linear model.

Hydrocortisone-Induced Stress

Fibroblasts (n=6) and lymphocytes (n=6) from patients with BD and age-matched controls (Fibroblasts, n=6; lymphocytes, n=6)) were exposed to hydrocortisone to induce mitochondrial stress (REFS). Hydrocortisone (Sigma H0888, St. Louis, Mo., USA) was dissolved in 50% ethanol/50% culture medium to yield a 40 mM stock solution. Hydrocortisone was then diluted to appropriate experimental concentrations (10 nM, 1 uM, 100 uM) with above described growth media. Confluent (85-95%) fibroblasts and lymphocytes ($1\times10^5$-$1\times10^6$) were treated for 24 hr with hydrocortisone (sub-acute stress). Cells treated with vehicle (25% ethanol) alone served as controls. Following hydrocortisone treatment, fibroblasts were examined for alterations in mitochondrial morphology, membrane potential, and ATP levels, as described above. All experiments were performed in triplicate.

Oxidative Stress

We also studied an equal number of fibroblast lines from BD and age-matched controls which were exposed to 100 μM hydrogen peroxide for 24 hrs (REFS). ATP levels were assayed as described above. Light microscopic analysis of JC1 to determine changes in mitochondrial membrane potential also were performed as previously described.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it can be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method for enhancing cardiac or cardiovascular function in a human subject in need thereof, said method comprising administering to said subject a pharmaceutical composition comprising isolated and substantially pure mitochondria in an amount sufficient to enhance said cardiac or cardiovascular function, wherein said mitochondria are syngeneic mitochondria or allogeneic mitochondria.

2. The method of claim 1, wherein said mitochondria are syngeneic mitochondria.

3. The method of claim 1, wherein said mitochondria are allogeneic mitochondria.

4. The method of claim 1, wherein said mitochondria are administered systemically.

5. A method for enhancing cardiac or cardiovascular function in a human subject in need thereof, said method comprising administering to said subject a pharmaceutical composition comprising isolated and substantially pure mitochondria in an amount sufficient to enhance said cardiac or cardiovascular function, wherein said mitochondria are administered locally into cardiac muscle.

6. The method of claim 1, wherein the isolated and substantially pure mitochondria are administered in an amount sufficient to increase the respiratory ability of a heart cell in the subject.

7. The method of claim 4, wherein the isolated and substantially pure mitochondria are administered in an amount sufficient to increase the respiratory ability of a heart cell in the subject.

8. The method of claim 5, wherein the isolated and substantially pure mitochondria are administered in an amount sufficient to increase the respiratory ability of a heart cell in the subject.

9. The method of claim 1, further comprising administering to said subject an agent selected from vitamin A, vitamin C, vitamin D, vitamin E, vitamin K, folic acid, choline, vitamin B1, vitamin B2, vitamin B5, vitamin B6, vitamin B12, biotin, nicotinamide, betacarotene, coenzyme Q, selenium, superoxide dismutase, glutathione peroxide, uridine, creatine succinate, pyruvate, dihydroxyacetone, acetyl-L-carnitine, alpha-lipoic acid, cardiolipin, omega fatty acid, lithium carbonate, lithium citrate, calcium, and mixtures thereof.

10. The method of claim 1, wherein the subject has a heart that is ischemic.

11. The method of claim 4, wherein the subject has a heart that is ischemic.

12. The method of claim 5, wherein the subject has a heart that is ischemic.

13. The method of claim 1, wherein the mitochondria are isolated from marrow-derived adult progenitor cells, stem cells, precursor cells, or skeletal muscle cells.

14. The method of claim 4, wherein the mitochondria are isolated from marrow-derived adult progenitor cells, stem cells, precursor cells, or skeletal muscle cells.

15. The method of claim 5, wherein the mitochondria are isolated from marrow-derived adult progenitor cells, stem cells, precursor cells, or skeletal muscle cells.

16. A method for enhancing cardiac or cardiovascular function in a human subject in need thereof, said method comprising administering to said subject a pharmaceutical composition comprising isolated and substantially pure mitochondria in an amount sufficient to enhance said cardiac or cardiovascular function, wherein the human subject has an ischemic heart tissue, and wherein said method comprises locally administering to said heart tissue a pharmaceutical composition comprising isolated and substantially pure syngeneic mitochondria in an amount sufficient to enhance cardiac or cardiovascular function of said subject.

17. The method of claim 16, wherein the isolated and substantially pure syngeneic mitochondria are administered in an amount sufficient to increase the respiratory ability of the heart cell or tissue.

18. The method of claim 16, wherein the mitochondria are isolated from skeletal muscle.

19. The method of claim 16, further comprising administering to said subject an agent selected from vitamin A, vitamin C, vitamin D, vitamin E, vitamin K, folic acid, choline, vitamin B1, vitamin B2, vitamin B5, vitamin B6, vitamin B12, biotin, nicotinamide, betacarotene, coenzyme Q, selenium, superoxide dismutase, glutathione peroxide, uridine, creatine succinate, pyruvate, dihydroxyacetone, acetyl-L-carnitine, alpha-lipoic acid, cardiolipin, omega fatty acid, lithium carbonate, lithium citrate, calcium, and mixtures thereof.

20. The method of claim 16, wherein the pharmaceutical composition is administered by local injection into cardiac muscle.

\* \* \* \* \*

UNITED STATES PATENT AND TRADEMARK OFFICE
CERTIFICATE OF CORRECTION

PATENT NO. : 9,855,296 B2
APPLICATION NO. : 15/353347
DATED : January 2, 2018
INVENTOR(S) : Anne M. Cataldo et al.

It is certified that error appears in the above-identified patent and that said Letters Patent is hereby corrected as shown below:

Column 3, Line 16, replace "ore" with --or--.

Column 11, Line 9, replace "without limitation bipolar disorder" with --without limitation, bipolar disorder--.

Column 15, Line 65, replace "a)" with --a--.

Column 17, Line 19, replace "propanamin ium" with --propanaminium--;
    Line 39, replace "phopatidylcholine" with --phosphatidylcholine--.

Column 19, Line 14, replace "pathognomic" with --pathognomonic--.

Column 25, Line 52, replace "Mitochondial" with --Mitochondrial--.

Column 28, Line 8, replace "oncoverslips" with --on coverslips--;
    Lines 43-46, replace "Briefly, cells were plated at a concentration of $2.5 \times 10^5$ cells per 60 mm dish were used for each experiment and experiments were conducted two days later" with --Briefly, cells were plated at a concentration of $2.5 \times 10^5$ cells per 60 mm dish and were used for each experiment, and experiments were conducted two days later--;
    Lines 48-49, replace "The cells then were centrifuges spun at 1000×g for 1 min." with --The cells then were centrifuged spun at 1000×g for 1 min.--.

Column 29, Line 12, replace "Fundations." with --Foundations.--.

Signed and Sealed this
Twenty-eighth Day of January, 2020

Andrei Iancu
*Director of the United States Patent and Trademark Office*